US007495111B2

(12) United States Patent
Ramamoorthy et al.

(10) Patent No.: US 7,495,111 B2
(45) Date of Patent: Feb. 24, 2009

(54) COMPOUNDS USEFUL AS SEROTONIN INHIBITORS AND 5-HT$_{1A}$ AGONISTS AND ANTAGONISTS

(75) Inventors: P. Sivaramakrishnan Ramamoorthy, West Windsor, NJ (US); Zhongqi Shen, Plainsboro, NJ (US); Boyd L. Harrison, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 86 days.

(21) Appl. No.: 11/453,364

(22) Filed: Jun. 15, 2006

(65) Prior Publication Data

US 2007/0149585 A1  Jun. 28, 2007

Related U.S. Application Data

(60) Provisional application No. 60/691,960, filed on Jun. 17, 2005.

(51) Int. Cl.
C07D 209/02 (2006.01)
C07D 209/56 (2006.01)
C07D 471/00 (2006.01)
C07D 335/08 (2006.01)
C07D 311/94 (2006.01)
A61K 31/445 (2006.01)
A61K 31/35 (2006.01)

(52) U.S. Cl. .................. 548/455; 548/400; 548/416; 548/427; 548/429; 548/430; 548/452; 548/454; 548/468; 546/26; 546/79; 546/80; 546/81; 546/84; 549/13; 549/23; 549/26; 549/200; 549/356; 549/381; 549/385; 549/387; 514/188; 514/277; 514/315; 514/319; 514/320; 514/321; 514/322; 514/359; 514/408; 514/430; 514/432; 514/444; 514/449; 514/451; 514/453; 514/454

(58) Field of Classification Search .......... 548/400, 548/416, 427, 429, 430, 452, 454, 455, 468; 546/26, 79, 80, 81, 84; 549/13, 23, 26, 200, 549/356, 381, 385, 387; 514/188, 277, 315, 514/319, 320, 321, 322, 359, 430, 432, 444, 514/449, 451, 453, 454, 408
See application file for complete search history.

(56) References Cited

U.S. PATENT DOCUMENTS

| | | | |
|---|---|---|---|
| 4,624,954 A | 11/1986 | Jirkovsky et al. | |
| 4,665,183 A | 5/1987 | Jirkovsky et al. | |
| 4,904,658 A | 2/1990 | Tseng et al. | |
| 5,219,857 A | 6/1993 | Tseng et al. | |
| 5,288,748 A | 2/1994 | Wikstrom et al. | |
| 6,084,130 A | 7/2000 | Romero et al. | |
| 6,127,357 A | 10/2000 | Cliffe et al. | |
| 6,465,482 B2 | 10/2002 | Mewshaw et al. | |
| 6,469,007 B2 | 10/2002 | Childers et al. | |
| 6,586,436 B2 | 7/2003 | Childers et al. | |
| 6,825,212 B2 | 11/2004 | Bernotas et al. | |
| 6,995,176 B2 | 2/2006 | Bernotas et al. | |
| 7,041,695 B2 | 5/2006 | Cole | |
| 2005/0032873 A1 | 2/2005 | Hatzenbuhler et al. | |

FOREIGN PATENT DOCUMENTS

| | | |
|---|---|---|
| WO | WO-97/03982 | 2/1997 |
| WO | WO-02/088132 | 11/2002 |
| WO | WO-02/088145 | 11/2002 |
| WO | WO-03/010169 | 2/2003 |
| WO | WO-03/087086 | 10/2003 |
| WO | WO-2004/024731 | 3/2004 |
| WO | WO-2004/099214 | 11/2004 |

OTHER PUBLICATIONS

Araneda, et al., "5-Hydroxytryptamine$_2$ and 5-Hydroxytryptamine$_{1A}$ Receptors Mediate Opposing Responses on Membrane Excitability in Rat Association Cortex", Neuroscience, 40(2):399-412 (1991).
Artigas, et al., "Acceleration of the Effect of Selected Antidepressant Drugs in Major Depression by 5-HT$_{1A}$ Antagonists", Trends Neurosci., 19(9):378-383 (1996).
Balducci, et al., "Reversal of Visual Attention Dysfunction after AMPA Lesions of the Nucleus Basalis Magnocellularis (NBM) by the Cholinesterase Inhibitor Donepezil and by a 5-HT$_{1A}$ Receptor Antagonist WAY 100635", Psychopharmacology, 167:28-36 (2003).
Blier, et al., "Effectiveness of Pindolol with Selected Antidepressant Drugs in the Treatment of Major Depression", J. Clin. Psychopharmacol., 15(3):217-222 (1995).
Blier, et al., "Modifications of the Serotonin System by Antidepressant Treatments: Implications for the Therapeutic Response in Major Depression", Journal of Clinical Psychopharmacology, 7(6 Suppl):24S-35S (1987).
Boast, et al., "5HT Antagonists Attenuate MK801-Impaired Radial Arm Maze Performance in Rats", Neurobiology of Learning and Memory, 71:259-271 (1999).
Bowen, et al., "Neurotransmission—the Link Integrating Alzheimer Research?", Trends in Neurosciences, 17(4):149-150 (1994).

(Continued)

*Primary Examiner*—Kamal A Saeed
*Assistant Examiner*—Samantha L Shterengarts
(74) *Attorney, Agent, or Firm*—Wilmer Cutler Pickering Hale and Dorr LLP

(57) ABSTRACT

3-Amino chroman and 2-amino tetralin derivatives and compositions containing such compounds are disclosed. Such compounds are useful for modulating activity of a 5-HT$_{1A}$ receptor (agonizing or antagonizing) in a patient. These compounds are further useful for inhibiting binding to a serotonin receptor. Methods of using the 3-amino chroman and 2-amino tetralin compounds and compositions containing such compounds in the treatment of serotonin disorders, such as depression and anxiety, are also disclosed.

42 Claims, No Drawings

OTHER PUBLICATIONS

Carli, et al., "WAY 100635, a 5-$HT_{1A}$ Receptor Antagonist, Prevents the Impairment of Spatial Learning Caused by Blockade of Hippocampal NMDA Receptors", Neuropharmacology, 38:1165-1173 (1999).

Carli, et al., "WAY 100635, a 5-$HT_{1A}$ Receptor Antagonist, Prevents the Impairment of Spatial Learning Caused by Intrahippocampal Administration of Scopolamine or 7-Chloro-Kynurenic Acid", Brain Research, 774:167-174 (1997).

Carli, et al., "(S)-WAY 100135, a 5-$HT_{1A}$ Receptor Antagonist, Prevents the Impairment of Spatial Learning Caused by Intrahippocampal Scopolamine", European Journal of Pharamcology, 283:133-139 (1995).

Childers, et al., "Synthesis and Biological Evaluation of Benzodioxanylpiperazine Derivatives as Potent Serotonin 5-$HT_{1A}$ Antagonists: The Discovery of Lecozotan", J. Med. Chem., 48:3467-3470 (2005).

Dijk, et al., "NMDA-Induced Glutamate and Aspartate Release from Rat Cortical Pyramidal Neurones: Evidence for Modulation By a 5-$HT_{1A}$ Antagonist", British Journal of Pharmacology, 115:1169-1174 (1995).

Dimitriou, "Buspirone Augmentation of Antidepressant Therapy", J. Clinical Psychopharmacol., 18(6):465-469 (1998).

Driver, et al., "A Second-Generation Catalyst for Aryl Halide Amination: Mixed Secondary Amines from Aryl Halides and Primary Amines Catalyzed by (DPPF)$PdCl_2$,", J. Am. Chem. Soc., 118:7217-7218 (1996).

Dunlop, et al., "Characterization of 5-$HT_{1A}$ Receptor Functional Coupling in Cells Expressing the Human 5-$HT_{1A}$ Receptor as Assesed with the Cytosensor Microphysiometer", Journal of Pharmacological and Toxicological Methods, 40:47-55 (1998).

Feiger, "A Double-Blind Comparison of Gepirone Extended Release, Imipramine, and Placebo in the Treatment of Outpatient Major Depression", Psychopharmacol. Bull., 32(4):659-665 (1996).

Grof, et al., "An Open Study of Oral Flesinoxan, a 5-$HT_{1A}$ Receptor Agonist, in Treatment-Resistant Depression", International Clinical Psychopharmacology, 8:167-172 (1993).

Harder, et al., "The 5-$HT_{1A}$ Antagonist, WAY 100 635, Alleviates Cognitive Impairments Induced by Dizocilpine (MK-801) in Monkeys", Neuropharmacology, 39:547-552 (2000).

Harder, et al., "The 5-$HT_{1A}$ Antagonist, WAY 100635, Ameliorates the Cognitive Impairment Induced by Fornix Transection in the Marmoset", Psychopharmacology, 127:245-254 (1996).

Hume, et al., "Evaluation of [O-methyl-$^3$H]WAY-100635 as an in vivo Radioligand for 5-$HT_{1A}$ Receptors in Rat Brain", European Journal of Pharmacology, 271:515-523 (1994).

Jones, "Synthesis of the Quinoline Ring System", Heterocylcic Compounds: vol. 32 (*Quinolines*), Chapter 2, Interscience, New York, pp. 93-318 (1977).

Matsuyama, et al., "Regulation of Glutamate Release via NMDA and 5-$HT_{1A}$ Receptors in Guinea Pig Dentate Gyrus", Brain Research, 728:175-180 (1996).

McLoughlin, et al., "Central Serotonergic Hyperresponsivity in Late-Onset Alzheimer's Disease", American Journal of Psychiatry, 151(11):1701-1703 (1994).

Perez, et al., "Randomised, Double-Blind, Placebo-Controlled Trial in Pindolol in Combination with Fluoxetine Antidepressant Treatment", The Lancet, 349:1594-1597 (1997).

Rabiner, et al., "5-Hydroxytryptamine$_{1A}$ Receptor Occupancy by Novel Full Antagonist 2-[4-[4-(7-Chloro-2,3-dihydro-1,4-benzdioxyn-5-yl)-1-piperazinyl]butyl]-1,2-benzisothiazol-3-(2H)-one-1,1-dioxide: A[$^{11}$C][Omethyl-3H]-N-(2-(4-(2-methoxyphenyl)-1-piperazinlyethyl)-N-(2-pyridinyl)cyclohexanecarboxamide Trihydrochloride (WAY-100635) Positron Emission Tomography Study in Humans", Journal of Pharmacology and Experimental Therapeutics, 301(3):1144-1150 (2002).

Sakai, et al., "Inhibitory Modulation of Long-Term Potentiation via the 5-$HT_{1A}$ Receptor in Slices of the Rat Hippocaompal Dentate Gyrus", Brain Research, 613:326-330 (1993).

Schechter, et al., "Lecozotan (SRA-333): A Selective Serotonin 1A Receptor Antagonist That Enhances the Stimulated Release of Glutamate and Acetylcholine in the Hippocampus and Possesses Cognitive-Enhancing Properties", Journal of Pharmacology and Experimental Therapeutics, 314(3):1274-1289 (2005).

Tome, et al., "Serotonergic Autoreceptor Blockade in the Reduction of Antidepressant Latency: Personality Variables and Response to Paroxetine and Pindolol", J. Affect Disord., 44:101-109 (1997).

Wilcox, et al., "A Double-Blind Trial of Low- and High-Dose Ranges of Gepirone-ER Compared with Placebo in the Treatment of Depressed Outpatients", Psychopharmacol. Bull., 32(3):335-342 (1996).

Wolfe, et al., "An Improved Catalyst System for Aromatic Carbon—Nitrogen Bond Formation: The Possible Involvement of Bis(Phosphine) Palladium Complexes as Key Intermediates", J. Am Chem. Soc., 118:7215-7216 (1996).

Yasuno, et al., "Inhibitory Effect of Hippocampal 5-$HT_{1A}$ Receptors on Human Explicit Memory", American Journal of Psychiatry, 160(2):334-340 (2003).

Yuen, et al., "Serotonin 5-$HT_{1A}$ Receptors Regulate NMDA Receptor Channels through a Microtubule-Dependent Mechanism", Journal of Neuroscience, 25(23):5488-5501 (2005).

Yoo, et al., "Synthesis of Heteroarylpiperazines and Heteroarylbipiperidines with a Restricted Side Chain and Their Affinities for 5-$HT_{1A}$ Receptor", Arch. Pharm. Pharm. Med. Chem., 336:208-215 (2003).

Invitation to Pay Additional Fees with Partial Search Report, issued for International Application No. PCT/US2006/022719, dated Apr. 20, 2007.

COMPOUNDS USEFUL AS SEROTONIN INHIBITORS AND 5-HT$_{1A}$ AGONISTS AND ANTAGONISTS

FIELD OF THE INVENTION

The present invention relates to novel 3-amino chroman and 2-amino tetralin derivatives, and in particular, to their use as both serotonin reuptake inhibitors and as 5-HT$_{1A}$ receptor agonists or antagonists, and to their related use for, inter alia, the treatment and/or prevention of depression and other conditions related to or affected by the reuptake of serotonin and the 5-HT$_{1A}$ receptor.

BACKGROUND OF THE INVENTION

Major depressive disorder affects an estimated 340 million people worldwide. Depression is the most frequently diagnosed psychiatric disorder and, according to the World Health Organization, is the fourth greatest public health problem. If left untreated, the effects of depression can be devastating, robbing people of the energy or motivation to perform everyday activities and, in some cases, leading to suicide. Symptoms of the disorder include feelings of sadness or emptiness, lack of interest or pleasure in nearly all activities, and feelings of worthlessness or inappropriate guilt. In addition to the personal costs of depression, the disorder also has been estimated to result in more than $40 billion in annual costs in the United States alone, due to premature death, lost productivity, and absenteeism.

Selective serotonin reuptake inhibitors (SSRIs) have had significant success in treating depression and related illnesses and have become among the most prescribed drugs since the 1980s. Some of the most widely known SSRIs are fluoxetine, sertraline, paroxetine, fluvoxamine and citalopram. Although they have a favorable side effect profile compared to tricyclic antidepressants (TCAs), they have their own particular set of side effects due to the non-selective stimulation of serotonergic sites. They typically have a slow onset of action, often taking several weeks to produce their full therapeutic effect. Furthermore, they have generally been found to be effective in less than two-thirds of patients.

SSRIs are believed to work by blocking the neuronal reuptake of serotonin, increasing the concentration of serotonin in the synaptic space, and thus increasing the activation of postsynaptic serotonin receptors. Although a single dose of a SSRI can inhibit the neuronal serotonin transporter, and thus would be expected to increase synaptic serotonin, clinical improvement has generally been observed only after long-term treatment. It has been suggested that the delay in onset of antidepressant action of the SSRIs is the result of an increase in serotonin levels in the vicinity of the serotonergic cell bodies. This excess serotonin is believed to activate somatodendritic autoreceptors, i.e., 5-HT$_{1A}$ receptors, reduce cell firing activity and, in turn, decrease serotonin release in major forebrain areas. This negative feedback limits the increment of synaptic serotonin that can be induced by antidepressants acutely. Over time, the somatodendritic autoreceptors become desensitized, allowing the full effect of the SSRIs to be expressed in the forebrain. This time period has been found to correspond to the latency for the onset of antidepressant activity [Perez, V., et al., *The Lancet*, 1997, 349: 1594-1597].

In contrast to the SSRIs, a 5-HT$_{1A}$ agonist or partial agonist acts directly on postsynaptic serotonin receptors to increase serotonergic neurotransmission during the latency period for the SSRI effect. Accordingly, the 5-HT$_{1A}$ partial agonists, buspirone and gepirone [Feiger, A., *Psychopharmacol. Bull.*, 1996, 32(4): 659-665; Wilcox, C., *Psychopharmacol. Bull.*, 1996, 32(93): 335-342], and the 5-HT$_{1A}$ agonist, flesinoxan [Grof, P., *International Clinical Psychopharmacology*, 1993, 8(3): 167-172], have shown efficacy in clinical trials for the treatment of depression. Furthermore, such agents are believed to stimulate the somatodendritic autoreceptors, thus hastening their desensitization and decreasing the SSRI latency period. An agent with a dual mechanism of antidepressant action would be expected to have greater efficacy and thus reduce the number of patients refractory to treatment. Indeed, buspirone augmentation to standard SSRI therapy has been shown to produce marked clinical improvement in patients initially unresponsive to standard antidepressant therapy [Dimitriou, E., *J. Clinical Psychopharmacol.*, 1998, 18(6): 465-469].

There is still an unfilled need for a single agent with a dual mechanism of antidepressant action, i.e., one that not only inhibits or blocks serotonin reuptake (to increase levels of serotonin in the synapse) but also antagonizes the 5-HT$_{1A}$ receptors (to reduce the latency period). The present invention is directed to these, as well as other important ends.

SUMMARY OF THE INVENTION

This invention relates to 3-amino chroman and 2-amino tetralin derivatives, and in particular, to methods of their use in the treatment and/or prevention of serotonin-related disorders, such as depression (including, but not limited to major depressive disorder, childhood depression and dysthymia), anxiety, panic disorder, post-traumatic stress disorder, premenstrual dysphoric disorder (also known as premenstrual syndrome), attention deficit disorder (with or without hyperactivity), obsessive-compulsive disorder, social anxiety disorder, generalized anxiety disorder, obesity, eating disorders such as anorexia nervosa and bulimia nervosa, vasomotor flushing, cocaine and alcohol addiction, sexual dysfunction, cognitive deficits resulting from neurodegenerative disorders like Alzheimer's disease, and related illnesses. Preferred compounds have the ability to bind 5-HT$_{1A}$ receptors, act as agonists, partial agonists or antagonists at the 5-HT$_{1A}$ receptors, and act as serotonin reuptake inhibitors.

In one aspect, the present invention provides 3-amino chroman and 2-amino tetralin derivatives of Formula (I):

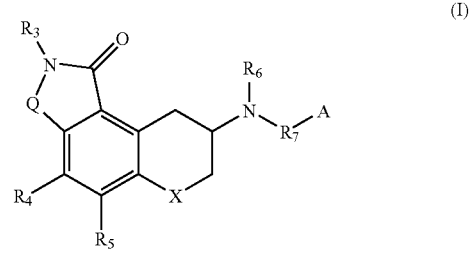

stereoisomer or pharmaceutically-acceptable salt thereof;

R$_3$ is a hydrogen, hydroxyl, halogen, —(C$_1$-C$_3$)-alkyl, —O—(C$_1$-C$_3$)-alkyl, —(C$_3$-C$_6$)-cycloalkyl, —SO$_2$R$_{20}$, or —COR$_{20}$, wherein —(C$_1$-C$_3$)-alkyl, —O—(C$_1$-C$_3$)-alkyl, or —(C$_3$-C$_6$)-cycloalkyl are optionally branched;

R$_4$ and R$_5$ are each independently hydrogen, hydroxyl, linear or branched —(C$_1$-C$_6$)-alkyl, linear or branched —(C$_2$-C$_6$)-alkenyl, halogen, —COR$_{14}$, —OR$_{14}$, —SR$_{14}$, —SO$_2$NR$_{14}$R$_{15}$, —NO$_2$, —CONR$_{14}$R$_{15}$ or —(C$_3$-C$_6$)-cycloalkyl, wherein one or two carbon atoms of the alkyl, alkenyl or cycloalkyl is optionally replaced by a nitrogen, oxygen or sulfur atom;

$R_6$ is hydrogen, a linear or branched —$(C_1$-$C_6)$-alkyl or a linear or branched —$(CH_2)_m$—B, wherein 1-3 carbon atoms of the —$(C_1$-$C_6)$-alkyl or —$(CH_2)_m$— chain may optionally be replaced by a nitrogen or oxygen atom, provided that $R_6$ has at least two carbon atoms in sequence (—$(C_1$-$C_2)$—) directly attached to the nitrogen of Formula (I), wherein B is a $(C_3$-$C_5)$-cycloalkyl, a saturated, partially saturated or aromatic $(C_5$-$C_7)$-carbocyclic ring or a phenyl fused to a saturated, partially saturated or aromatic $(C_5$-$C_7)$-carbocyclic ring, wherein the cycloalkyl, phenyl or carbocyclic ring is optionally substituted by one to two substituents per ring, wherein said substituents are independently selected from the group consisting of halogen, cyano, —$(C_1$-$C_6)$-alkyl, —$(C_2$-$C_6)$-alkenyl, —$(C_2$-$C_6)$-alkynyl, —$(C_3$-$C_7)$-carbocycle, —$(C_1$-$C_6)$-alkoxy, —$OCF_3$, —$(C_6$-$C_{10})$-aryl and —$(C_2$-$C_9)$-heterocycle; further wherein one or two ring atoms in the cycloalkyl, phenyl or carbocyclic ring may optionally be replaced by a nitrogen, oxygen or sulfur atom, and m is a number from 0 to 7;

$R_7$ is selected from a linear or branched —$(C_1$-$C_6)$-alkylene-, linear or branched —$(C_2$-$C_6)$-alkenylene- or —$(CH_2)_p$—$(C_3$-$C_6)$-cycloalkyl-$(CH_2)_q$—, each of which is optionally substituted with a halogen or hydroxyl, wherein at least one ring atom of the —$(C_3$-$C_6)$-cycloalkyl is optionally replaced by a nitrogen, sulfur or oxygen, and at least two ring atoms of the alkylene, alkenylene or cycloalkyl are carbon atoms, and p and q are each independently 0, 1 or 2;

Q is selected from —$(C_1$-$C_3)$-alkylene-, —O—$(C_1$-$C_2)$-alkylene-, —$(C_2$-$C_3)$-alkenylene-, or —O—$(C_2)$-alkenylene-, wherein the alkylene or alkenylene is optionally substituted with a —$(C_1$-$C_3)$-alkyl or a halogen, and wherein for —O—$(C_1$-$C_2)$-alkylene- or —O—$(C_2$-$C_3)$-alkenylene-, the O is directly attached to the phenyl ring;

A is

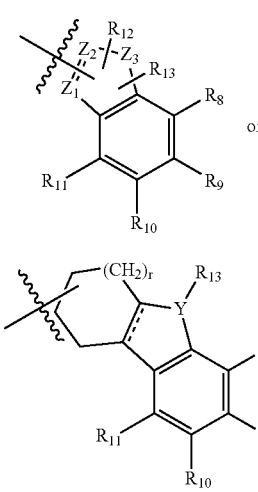

(A$_1$)

(A$_2$)

$R_8$, $R_9$, $R_{10}$, and $R_{11}$ are each independently hydrogen, cyano, carboxamido, carboalkoxy, trifluoromethyl, hydroxyl, linear or branched —$(C_1$-$C_6)$-alkyl, linear or branched —$(C_2$-$C_6)$-alkenyl, halogen, —$OCF_3$, alkanoyloxy, alkanamido, alkanesulfonyl, alkanesulfonamido, phenyl, —$NR_{16}R_{17}$, -, —$COR_{16}$, —$OR_{16}$, —$SR_{16}$, —$OR_{16}$, or —$NO_2$, W, X and Y are each independently —$CR_{18}R_{19}$—, —O—, —$NR_{18}$— or —S—;

X and Y are each independently —$CR_{18}R_{19}$—, —O—, —$NR_{18}$— or —S—;

$Z_1$ is carbon or nitrogen, $Z_2$ is carbon and $Z_3$ is carbon, nitrogen, oxygen or sulfur; wherein at least one of $Z_1$ and $Z_3$ is not carbon, wherein a double bond is optionally present between $Z_1$ and $Z_2$, wherein $A_1$ is attached to $R_7$ through $Z_1$, $Z_2$ or $Z_3$ except when $Z_3$ is oxygen, and further wherein when $R_7$ is linked to $Z_3$, then $Z_3$ is nitrogen;

$R_{12}$ and $R_{13}$ are each independently hydrogen or a linear or branched —$(C_1$-$C_6)$-alkyl, wherein $R_{12}$ and $R_{13}$ may be attached at any of $Z_1$, $Z_2$ or $Z_3$, and further wherein $R_{13}$ is optionally present at $Z_1$ or $Z_2$ when $Z_3$ is oxygen;

$R_{14}$, $R_{15}$, $R_{16}$, $R_{17}$, $R_{18}$ and $R_{19}$ are each independently hydrogen, hydroxyl, halogen, a linear or branched $(C_1$-$C_6)$-alkyl or a linear or branched $(C_2$-$C_6)$-alkenyl; $R_{20}$ is a hydrogen, a linear or branched $(C_1$-$C_6)$-alkyl or a $(C_3$-$C_7)$-cycloalkyl; and the dotted lines represent optional double bonds.

In preferred embodiments, in the compound of Formula (I), where A is $A_2$, Y is —NH— or —O—. Alternatively, in preferred embodiments in the compound of Formula (I), where A is $A_1$, $R_7$ is linked at $Z_1$, $Z_3$ is —N—, $R_{13}$ is hydrogen or —$CH_3$, and a double bond is present between $Z_1$ and $Z_2$. In additional preferred embodiments, where A is $A_1$, $Z_1$ is carbon, $Z_3$ is —O—, $R_{13}$ is not present, and a double bond is present between $Z_1$ and $Z_2$.

In addition, preferred are compounds according to claim 1 of Formula (I), wherein X is —O—.

Further preferred are compounds of Formula (I) wherein $R_6$ is selected from:

—$(CH_2)_m$—B, m is 0 or 1, and B is a $C_3$-$C_6$-cycloalkyl, a linear $C_2$-$C_4$-alkyl, or a branched $C_3$-$C_5$-alkyl, —$(CH_2)_m$—B, m is 0 or 1, and B is an aromatic $(C_5$-$C_7)$-carbocyclic ring, wherein one to two ring atoms may optionally be replaced by an oxygen, and —$(CH_2)_m$—B, m is 2, 3 or 4, and B is a phenyl fused to a saturated, partially saturated or aromatic $(C_5$-$C_7)$-carbocyclic ring, wherein the phenyl or carbocyclic ring is optionally substituted by one to two halogen atoms, further wherein one to two ring atoms of the $(C_5$-$C_7)$-carbocyclic ring may optionally be replaced by a nitrogen or oxygen atom.

In preferred compounds of Formula (I), A is

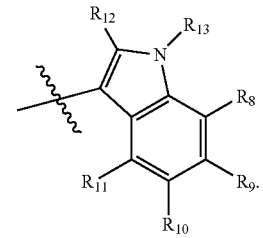

Alternatively, in preferred embodiments, A is

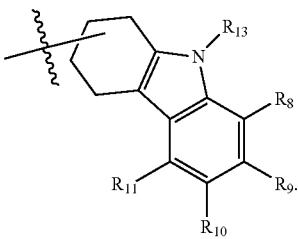

In addition, preferred are compounds of Formula (I), wherein A is

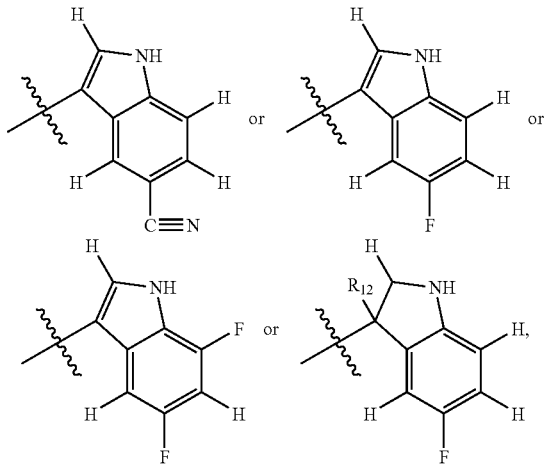

wherein $R_{12}$ is a linear —$(C_1$-$C_6)$-alkyl, preferably methyl or ethyl.

Also preferred are compounds of Formula (I), wherein A is

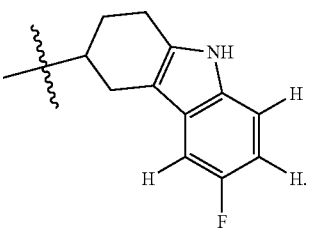

In preferred embodiments of compounds of Formula (I), at least one of $R_5$, $R_8$, $R_9$, $R_{10}$ and $R_{11}$ is fluorine. In particular embodiments, $R_8$, $R_9$, and $R_{11}$ are hydrogen and $R_{10}$ is fluorine.

Further, $R_3$ is preferably —$CH_3$ or hydrogen, and more preferably —$CH_3$ in particular embodiments.

Q is preferably —$CH_2$—, —$(CH_2)_2$—, —O—$(CH_2)_2$—, —O—$(CH_2)_2$—, —$CH_2$=$CH_2$— or —O—$CH_2$=$CH_2$—.

Preferably, in the compound of Formula (I), $R_4$ or $R_5$ is —O—$CH_2$ or —$NO_2$. In additional embodiments, $R_4$ is preferably hydrogen. Further embodiments include $R_5$ preferably being —$OR_{14}$, halogen or hydrogen and in particular, $R_5$ being —$OCH_3$.

$R_7$ is preferably a linear —$(C_1$-$C_4)$-alkylene- or —$(CH_2)_p$—$(C_3$-$C_6)$-cycloalkyl-$(CH_2)_q$—. In further preferred embodiments, $R_7$ is

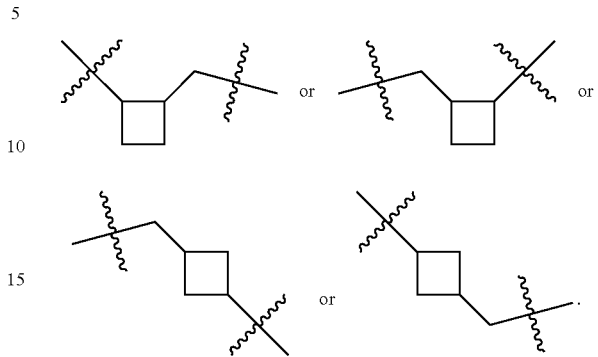

Further preferred, are compounds of Formula (I), wherein $R_{10}$ is a nitrile group.

In some preferred embodiments, the present invention provides compounds of Formula (Ia):

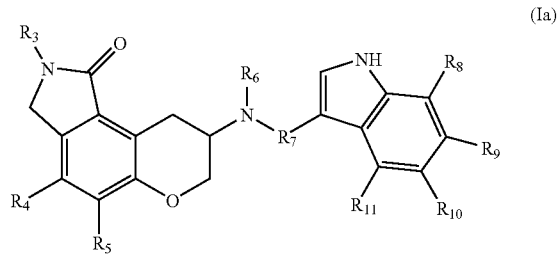

(Ia)

wherein $R_3$, $R_4$, $R_5$, $R_6$, $R_7$, $R_8$, $R_9$, $R_{10}$ and $R_{11}$ are as previously defined, or a prodrug, stereoisomer or pharmaceutically-acceptable salt thereof.

In other preferred embodiments, the present invention is directed to compounds of Formula (Ib)

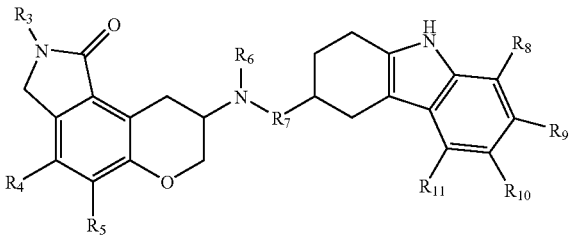

(Ib)

wherein $R_3$, $R_4$, $R_5$, $R_6$, $R_7$, $R_8$, $R_9$, $R_{10}$ and $R_{11}$, are as previously defined, or a prodrug, stereoisomer or pharmaceutically-acceptable salt thereof.

In additional embodiments, the compounds are of Formula (Ic)

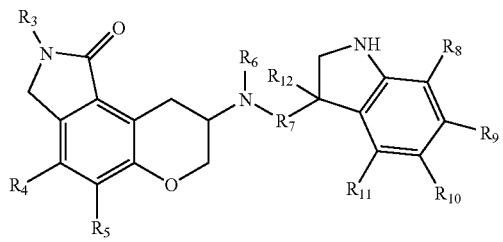
(Ic)

wherein $R_3$, $R_4$, $R_5$, $R_6$, $R_7$, $R_8$, $R_9$, $R_{10}$, $R_{11}$ and $R_{12}$ are as previously defined, or a prodrug, stereoisomer or pharmaceutically-acceptable salt thereof. Particular embodiments include at least one of the following: $R_3$, $R_4$, $R_8$, $R_9$ and $R_{11}$ are hydrogen; $R_5$ is —$OCH_3$ or fluorine; $R_6$ is —$(CH_2)_m$—B, with —B being a —$(C_3\text{-}C_5)$-cycloalkyl (in particular where m is 1 and B is a $C_4$-cycloalkyl ring, i.e., cyclobutyl ring); $R_7$ is —$(CH_2)_p$—$(C_3\text{-}C_6)$-cycloalkyl-$(CH_2)_q$— (particularly where p is 0 and q is 1 or p is 1 and q is 0, and the cycloalkyl is a —$C_4$-cycloalkyl-, i.e., -cyclobutyl-); $R_{10}$ is a halogen, preferably fluorine; and $R_{12}$ is a —$(C_1\text{-}C_6)$-alkyl, preferably a methyl or ethyl group.

In another embodiment, the present invention is directed to the compounds or a prodrug, stereoisomer or pharmaceutically-acceptable salt thereof of the compound of Formula (I) or Formula (Ia) or Formula (Ib) or Formula (Ic) and one or more pharmaceutically acceptable carriers.

In one embodiment, the compounds or pharmaceutically acceptable salts of the compounds of the Formula (I) or Formula (Ia) or Formula (Ib) or Formula (Ic) are useful as serotonin reuptake inhibitors.

In a further embodiment, the compounds or pharmaceutically acceptable salts of the compounds of the Formula (I) or Formula (Ia) or Formula (Ib) or Formula (Ic) are useful as agonists and/or antagonists of 5-$HT_{1A}$ receptors.

The present invention also provides methods of treating and/or preventing a serotonin-related disorder in a patient suspected of suffering from a serotonin-related disorder, comprising the step of administering to the patient a therapeutically effective amount of a compound of Formula (I) or Formula (Ia) or Formula (Ib). In a further embodiment, the present invention provides methods for treating and/or preventing depression (including, but not limited traumatic stress disorder, premenstrual dysphoric disorder (also known as premenstrual syndrome), attention deficit disorder (with or without hyperactivity), obsessive compulsive disorder, social anxiety disorder, generalized anxiety disorder, obesity, eating disorders such as anorexia nervosa and bulimia nervosa, vasomotor flushing, cocaine and alcohol addiction, sexual dysfunction, cognitive deficits resulting from neurodegenerative disorders like Alzheimer's disease, and related illnesses.

In another embodiment, the present invention is directed to methods of inhibiting the reuptake of serotonin in a patient in need thereof, comprising the step of administering to the patient a therapeutically effective amount of a compound of Formula (I) or Formula (Ia) or Formula (Ib).

The present invention is also directed to a method of agonizing and/or antagonizing 5-$HT_{1A}$ receptors in a patient in need thereof, comprising the step of administering to the patient a therapeutically effective amount of a compound of Formula (I) or Formula (Ia) or Formula (Ib).

The present invention further relates to a method of making a compound of the invention of Formula (I), wherein said method comprises (a) nitrating a compound of formula (II)

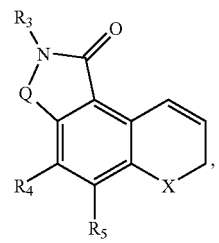
(II)

(b) reducing the compound to provide a compound of formula (III)

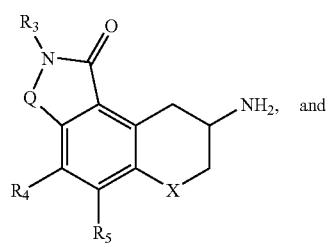
(III)

(c) subjecting the compound of formula (III) to reductive amination with an aldehyde of formula (IV)

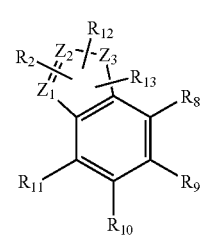
(IV)

wherein $R_2$ is the corresponding aldehyde of $R_7$ under conditions sufficient to produce a compound of formula

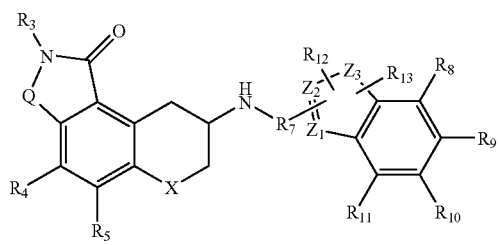
(V)

wherein said compound of formula (V) is optionally subjected to an alkylation in the presence of a base under conditions effective to produce a compound of formula (VI)

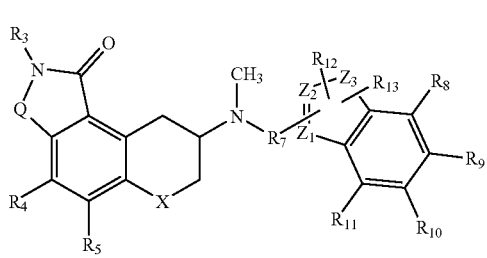

(VI)

or is optionally subjected to a reductive amination by reacting with a compound of formula $R_6CHO$ to produce a compound of formula (VII)

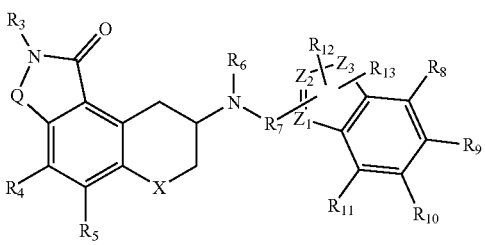

(VII)

Further encompassed is a method of making a compound of the invention of Formula (I), wherein said method comprises (a) combining a compound of formula (III)

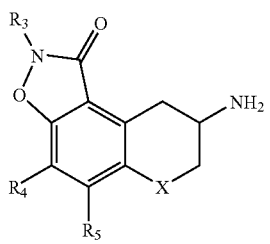

(III)

with a compound of formula (VIII)

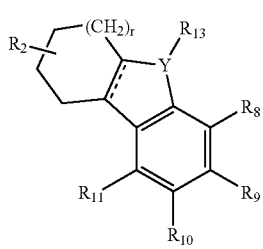

(VIII)

wherein $R_2$ is the corresponding amine of $R_7$, under conditions sufficient for reductive amination;

(b) combining the product of (a) with a compound of formula $R_6CHO$ under conditions for reductive amination, to obtain a compound of formula (IX)

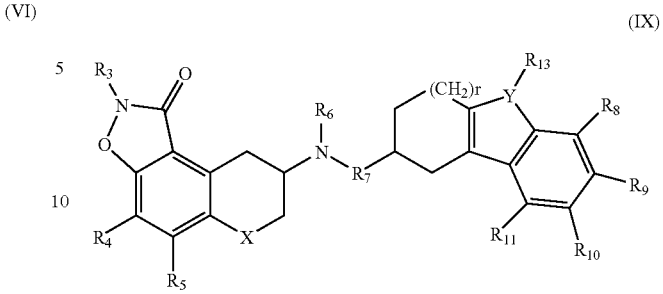

(IX)

Preferably, the method further comprises the step of alkylating the compound of formula (II) with an alkyl halide under conditions sufficient to produce a compound of formula (IIa)

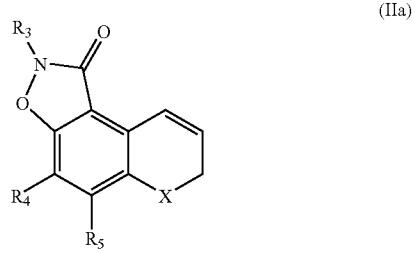

(IIa)

prior to step (b), wherein $R_3$ is a $—(C_1-C_3)$-alkyl.

The instant invention further provides a method of making a compound of formula (XII)

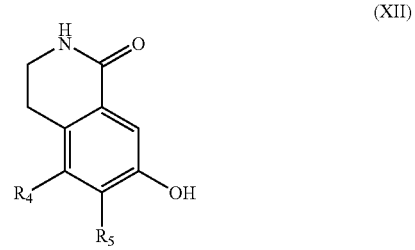

(XII)

wherein said method comprises (a) subjecting a compound of formula (X)

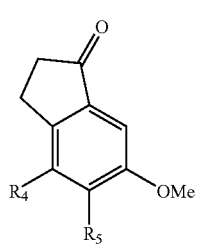

(X)

to a rearrangement reaction under conditions sufficient to produce a compound of formula (XI)

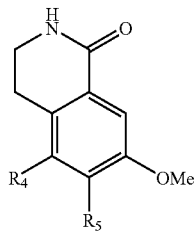

(XI)

(b) isolating the compound of formula (XI),
(c) deprotecting the compound of formula (XI) to produce a compound of formula (XII)

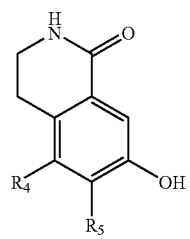

(XII)

The present invention further includes a method whereby the compound of formula (XII) is subject to a propargylating reaction under conditions sufficient to produce a compound of formula (XIIa)

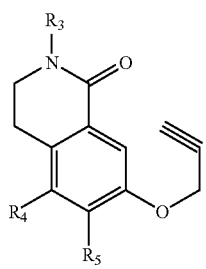

(XIIa)

subjecting the compound of formula (XIIa) to a cyclization reaction under conditions sufficient to produce a compound of formula (XIII)

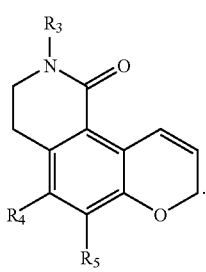

(XIII)

Preferably, $R_3$ is hydrogen or a —($C_1$-$C_3$) alkyl. For $R_3$ to be an alkyl, for example, the compound is alkylated by reaction with an alkyl halide under conditions sufficient to substitute $R_3$ for H. Other methods known in the art may be used to substitute additional $R_3$ groups.

Additionally, the invention provides a method of making a compound of Formula (I), wherein said method comprises
(a) nitrating a compound of formula (XIII)

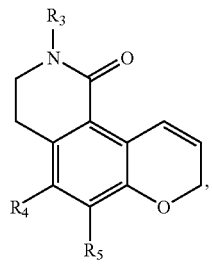

(XIII)

(b) reducing the compound to produce a compound of formula (XIV)

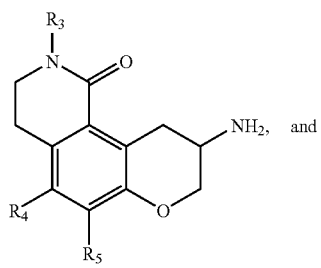

(XIV)

(c) subjecting the compound of formula (XIV) to reductive amination with an aldehyde of formula (IV)

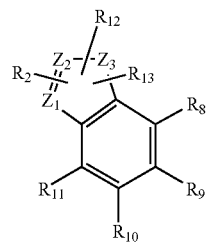

(IV)

wherein $R_2$ is the corresponding aldehyde of $R_7$ under conditions sufficient to produce a compound of formula (XV)

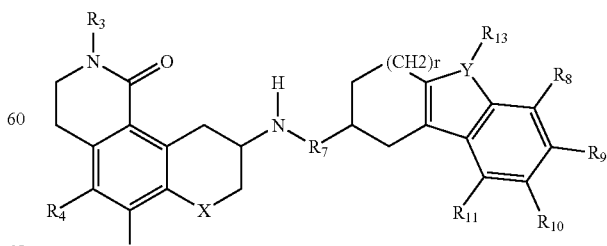

(XV)

wherein said compound of formula (XV) is optionally subjected to an alkylation in the presence of a base under conditions effective to produce a compound of formula (XVI)

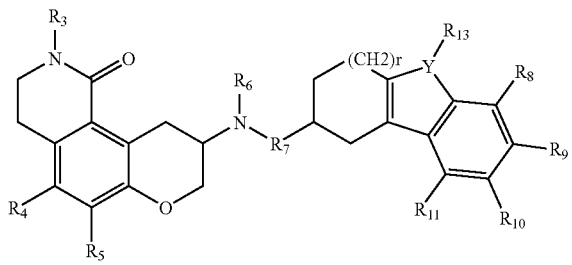
(XVI)

wherein $R_6$ is a —($C_1$-$C_3$)-alkyl, or is optionally subjected to a reductive amination by reacting with a compound of formula $R_6$CHO to produce a compound of formula (XVII)

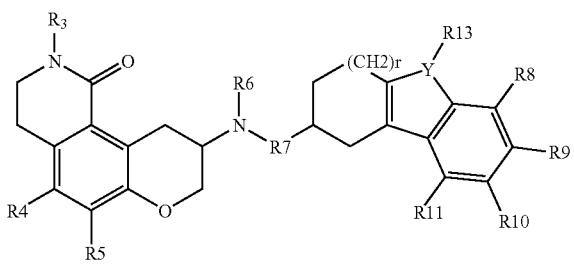
(XVII)

wherein $R_6$ is as defined in claim 1.

The invention further provides a method of making a compound of Formula (I), wherein the method comprises (a) combining a compound of formula (XIV)

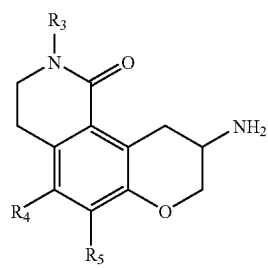
(XIV)

with a compound of formula (VIII)

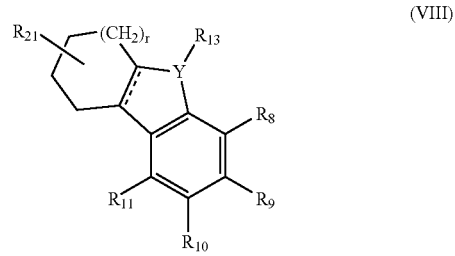
(VIII)

under conditions for reductive amination;

(b) combining the product of (a) with a compound of formula $R_6$CHO under conditions for reductive amination, to obtain a compound of formula (XVI)

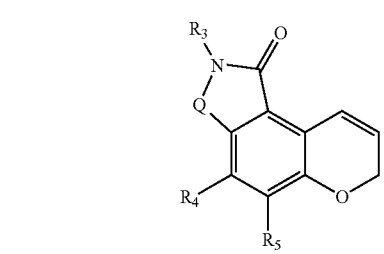
(XVI)

The present invention further provides a method of making a compound of formula (IIb)

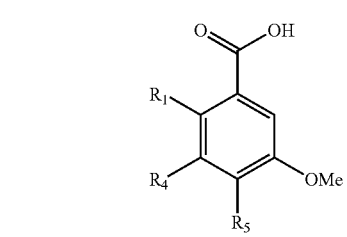
(IIb)

comprising (a) protecting a carboxylic acid of formula (XVII)

(XVII)

wherein $R_1$ is —Br, —Cl or —OSO$_2$CF$_3$, by alkylation under conditions sufficient to produce a compound of formula (XVIII)

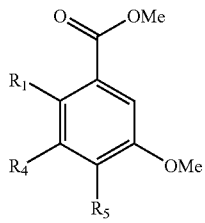

(XVIII)

(b) replacing $R_1$ with a methyl group to produce a compound of formula (XIX)

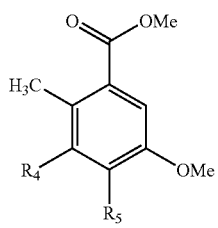

(XIX)

(c) halogenating the compound of formula (XIX) and heating under conditions sufficient to produce a compound of formula (XX)

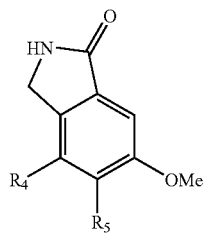

(XX)

(d) deprotecting the compound of formula (XX) under conditions sufficient to produce a compound of formula (XXI)

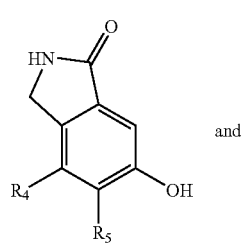

(XXI)

and (e) propargylating under conditions sufficient to produce a compound of formula (XXII)

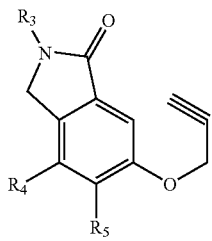

(XXII)

(f) subjecting the compound of formula (XXII) to a cyclization reaction under conditions sufficient to produce a compound of formula (IIb)

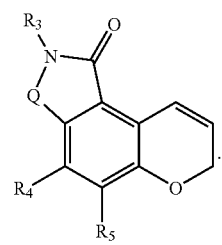

(IIb)

Preferably, $R_3$ is hydrogen or a —(C$_1$-C$_3$) alkyl. For $R_3$ to be an alkyl, for example, the compound may be alkylated by reaction with an alkyl halide under conditions sufficient to substitute $R_3$ for H. Other methods known in the art may be used to substitute additional $R_3$ groups.

A method for making a compound of formula (XXIII)

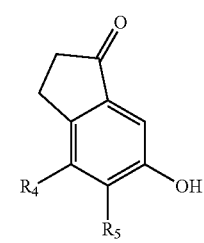

(XXIII)

comprising (a) reacting a compound of formula (XXIV)

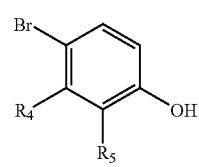

(XXIV)

with a compound of formula (XXV)

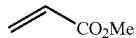
(XXV)

under conditions sufficient to produce a compound of formula (XXVI)

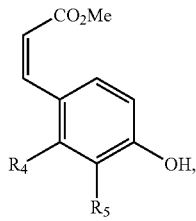
(XXVI)

(b) reducing the compound of formula (XXVI) to produce a saturated methyl ester of formula (XXVII)

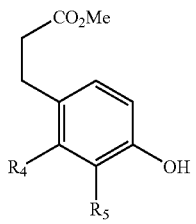
(XXVII)

(c) hydrolyzing the ester under conditions sufficient to provide a carboxylic acid of formula (XXVIII)

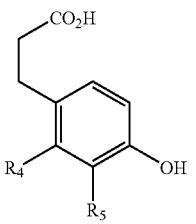
(XXVIII)

(d) cyclyzing the carboxylic acid by heating in the presence of a Lewis acid under conditions sufficient to provide a compound of formula (XXIX)

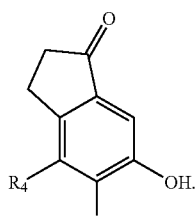
(XXIX)

The invention further provides a method, which method is further comprising (e) subjecting the compound of formula (XXIX) to a rearrangement reaction under reaction conditions sufficient to produce a compound of formula (XXX)

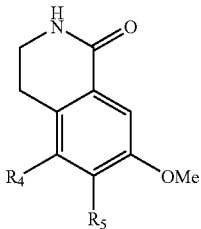
(XXX)

(b) isolating the compound of formula (XXX), (c) deprotecting the compound of formula (XXX) to produce a compound of formula (XXXI)

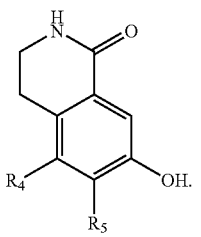
(XXXI)

A compound of formula XXXI may optionally be substituted with $R_3$ as defined in Formula I by methods known by those skilled in the art.

It should be understood that these preferred processes may be modified in accordance with ordinary skill in the art.

DETAILED DESCRIPTION OF ILLUSTRATIVE EMBODIMENTS (a) Definitions

The term "($C_1$-$C_6$)-alkyl" as used herein refers to a linear or branched, saturated hydrocarbon having from 1 to 6 carbon atoms. Representative ($C_1$-$C_6$)-alkyl groups include, but are not limited to, methyl, ethyl, propyl, isopropyl, butyl, sec-butyl, tert-butyl, pentyl, isopentyl, neopentyl, hexyl, isohexyl, and neohexyl. In one embodiment, the ($C_1$-$C_6$)-alkyl group is substituted with one or more of the following groups: halogen, —$N_3$, —$NO_2$, —CN, —OR', —SR', —$SO_2$R', —$SO_2$N(R')$_2$, —N(R')$_2$, —COR', —$CO_2$R', —NR'$CO_2$R', —NR'COR', —NR'CONR', or —CON(R')$_2$, wherein each R' is independently hydrogen or unsubstituted ($C_1$-$C_6$)-alkyl.

The term "($C_2$-$C_6$)-alkenyl" as used herein refers to a linear or branched hydrocarbon having from 2 to 6 carbon atoms and having at least one carbon-carbon double bond. In one embodiment, the ($C_2$-$C_6$)-alkenyl has one or two double bonds. The ($C_2$-$C_6$)-alkenyl moiety may exist in the E or Z conformation and the compounds of the present invention include both conformations. In one embodiment, the ($C_2$-$C_6$)-alkenyl group is substituted with one or more of the following groups: halogen, —$N_3$, —$NO_2$, —CN, —OR', —SR', —$SO_2$R', —$SO_2$N(R')$_2$, —N(R')$_2$, —COR', —$CO_2$R', —NR'CO$_2$R', —NR'COR', —NR'CONR', or —CON(R')$_2$, wherein each R' is independently hydrogen or unsubstituted (C$_1$-C$_6$)-alkyl.

The term "(C$_2$-C$_6$)-alkynyl" as used herein refers to a linear or branched hydrocarbon having from 2 to 6 carbon atoms and having at least one carbon-carbon triple bond. In one embodiment, the (C$_2$-C$_6$)-alkynyl group is substituted with one or more of the following groups: halogen, —N$_3$, —NO$_2$, —CN, —OR', —SR', —SO$_2$R', —SO$_2$N(R')$_2$, —N(R')$_2$, —COR', —CO$_2$R', —NR'CO$_2$R', —NR'COR', —NR'CONR', or —CON(R')$_2$, wherein each R' is independently hydrogen or unsubstituted (C$_1$-C$_6$)-alkyl.

The term "administer", "administering", or "administration", as used herein refers to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of active compound within the animal's body.

The term "animal" as used herein includes, without limitation, a human, mouse, rat, guinea pig, dog, cat, horse, cow, pig, monkey, chimpanzee, baboon, or rhesus. In one embodiment, the animal is a mammal. In another embodiment, the animal is a human.

The term "aryl" as used herein refers to an aromatic species containing 1 to 3 aromatic rings, either fused or linked. In one embodiment, the aryl group is substituted with one or more of the following groups: VH, —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', or —V—CON(R')$_2$, wherein each R' is independently hydrogen or unsubstituted (C$_1$-C$_6$)-alkyl; and wherein each V is independently a bond or (C$_1$-C$_6$)-alkyl.

The term "conditions effective to" as used herein refers to synthetic reaction conditions which will be apparent to those skilled in the art of synthetic organic chemistry.

The term "cyclic group" as used herein includes a cycloalkyl group and a heterocyclic group. Any suitable ring position of the cyclic group may be covalently linked to the defined chemical structure. In one embodiment, the cyclic group is substituted with one or more of the following groups: VH, —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', or —V—CON(R')$_2$, wherein each R' is independently hydrogen or unsubstituted (C$_1$-C$_6$)-alkyl; and wherein each V is independently a bond or (C$_1$-C$_6$)-alkyl.

The term "cycloalkyl group" as used herein refers to a three- to seven-membered saturated or partially unsaturated carbon ring. Any suitable ring position of the cycloalkyl group may be covalently linked to the defined chemical structure. Exemplary cycloalkyl groups include cyclopropyl, cyclobutyl, cyclopentyl, cyclohexyl, and cycloheptyl. In one embodiment, the cycloalkyl group is substituted with one or more of the following groups: VH, —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', or —V—CON(R')$_2$, wherein each R' is independently hydrogen or unsubstituted (C$_1$-C$_6$)-alkyl; and wherein each V is independently a bond or (C$_1$-C$_6$)-alkyl.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "carrier", as used herein, shall encompass carriers, excipients, and diluents.

The term "prodrug", as used herein means a compound which is convertible in vivo by metabolic means (e.g. by hydrolysis) to a compound of Formula (I), (Ia) or (Ib).

The term "halogen" as used herein refers to fluorine, chlorine, bromine, and iodine.

The term "heterocyclic group" as used herein refers to a three- to seven-membered saturated, partially saturated, or unsaturated cycloalkyl group in which one to four of the ring carbon atoms have been independently replaced with a N, O, or S atom. Any suitable ring position of the heterocyclic group may be covalently linked to the defined chemical structure. Exemplary heterocyclic groups include, but are not limited to, azepanyl, azetidinyl, aziridinyl, furanyl, furazanyl, homopiperazinyl, imidazolidinyl, imidazolinyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, and triazolyl. In one embodiment, the heterocyclic group is substituted with one or more of the following groups: VH, —V-halogen, —V—N3, —V—NO2, —V—CN, —V—OR', —V—SR', —V—SO2R', —V—SO2N(R')2, —V—N(R')2, —V—COR', —V—CO2R', —V—NR'CO2R', —V—NR'COR', —V—NR'CONR', or —V—CON(R')2, wherein each R' is independently hydrogen or unsubstituted (C1-C6)-alkyl; and wherein each V is independently a bond or (C1-C6)-alkyl.

The term "isolated and purified" as used herein refers to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The term "pharmaceutically acceptable salt" as used herein refers to a salt of an acid and a basic nitrogen atom of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the present invention.

The term "phenyl" as used herein refers to a substituted or unsubstituted phenyl group. In one embodiment, the phenyl group is substituted with one or more of the following groups: VH, —V—halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', or —V—CON(R')$_2$, wherein each R' is independently hydrogen or unsubstituted ($C_1$-$C_6$)-alkyl; and wherein each V is independently a bond or ($C_1$-$C_6$)-alkyl.

The term "substantially free of its corresponding opposite enantiomer" as used herein means that the compound contains no more than about 10% by weight of its corresponding opposite enantiomer. In other embodiments, the compound that is substantially free of its corresponding opposite enantiomer contains no more than about 5%, no more than about 1%, no more than about 0.5%, or no more than about 0.1% by weight of its corresponding opposite enantiomer. An enantiomer that is substantially free of its corresponding opposite enantiomer includes a compound that has been isolated and purified or has been prepared substantially free of its corresponding opposite enantiomer.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

(b) Compounds and Pharmaceutically Acceptable Salts of Compounds of the Invention In one embodiment, the present invention is directed to compounds of the Formula (I):

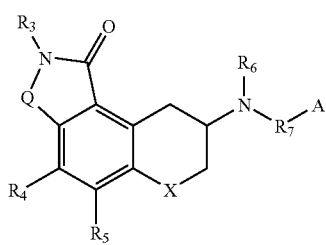

(I)

or a prodrug, stereoisomer or pharmaceutically-acceptable salt thereof, wherein $R_3$ is a hydrogen, hydroxyl, halogen, —($C_1$-$C_3$)-alkyl, —O—($C_1$-$C_3$)-alkyl, —($C_3$-$C_6$)-cycloalkyl, —$SO_2R_{20}$, or —$COR_{20}$, wherein —($C_1$-$C_3$)-alkyl, —O—($C_1$-$C_3$)-alkyl, or —($C_3$-$C_6$)-cycloalkyl are optionally branched.

$R_4$ and $R_5$ are each independently hydrogen, hydroxyl, linear or branched —($C_1$-$C_6$)-alkyl, linear or branched —($C_2$-$C_6$)-alkenyl, halogen, —$COR_{14}$, —$OR_{14}$, —$SR_{14}$, —$SO_2NR_{14}R_{15}$, —$NO_2$, —$CONR_{14}R_{15}$ or —($C_3$-$C_6$)-cycloalkyl, which optionally contains a nitrogen, oxygen or sulfur atom;

$R_6$ is hydrogen, a linear or branched —($C_1$-$C_6$)-alkyl or a linear or branched —(CH$_2$)$_m$—B, the —($C_1$-$C_6$)-alkyl or —(CH$_2$)$_m$—B which may optionally be substituted with at least one nitrogen or oxygen atom provided that $R_6$ has at least two carbon atoms in sequence directly attached to the nitrogen of Formula (I), wherein B is a ($C_3$-$C_5$)-cycloalkyl, a saturated, partially saturated or aromatic ($C_5$-$C_7$)-carbocyclic ring or a phenyl fused to a saturated, partially saturated or aromatic ($C_5$-$C_7$)-carbocyclic ring, wherein the cycloalkyl, phenyl or carbocyclic ring is optionally substituted by one to two substituents per ring, wherein said substituents are independently selected from the group consisting of halogen, cyano, —($C_1$-$C_6$)-alkyl, —($C_2$-$C_6$)-alkenyl, —($C_2$-$C_6$)-alkynyl, —($C_3$-$C_7$)-carbocycle, —($C_1$-$C_6$)-alkoxy, —$OCF_3$, —($C_6$-$C_{10}$)-aryl and —($C_2$-$C_9$)-heterocycle; further wherein one or two ring atoms of the cycloalkyl, phenyl or carbocyclic ring may optionally be replaced by a nitrogen, oxygen or sulfur atom, and m is a number from 0 to 7;

$R_7$ is selected from a linear or branched —($C_1$-$C_6$)-alkylene-, linear or branched —($C_2$-$C_6$)-alkenylene- or —(CH$_2$)$_p$—($C_3$-$C_6$)-cycloalkyl-(CH$_2$)$_q$—, each of which is optionally substituted with a halogen or hydroxyl, wherein one or two ring atoms of the cycloalkyl may optionally replaced by a nitrogen, sulfur or oxygen atom, and p and q are each independently 0, 1 or 2;

Q is selected from —($C_1$-$C_3$)-alkylene-, —O—($C_1$-$C_2$)-alkylene-, —($C_2$-$C_3$)-alkenylene-, or —O—$C_2$)-alkenylene-, wherein the alkylene or alkenylene is optionally substituted with a —($C_1$-$C_3$)-alkyl or a halogen, and wherein for —O—($C_1$-$C_2$)-alkylene- or —O—($C_2$-$C_3$)-alkenylene-, the O is directly attached to the phenyl ring;

A is

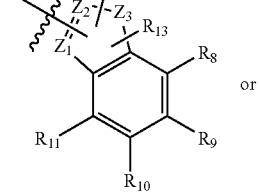

($A_1$)

or

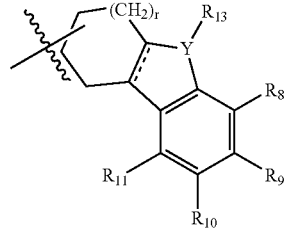

($A_2$)

$R_8$, $R_9$, $R_{10}$, and $R_{11}$ are each independently hydrogen, cyano, carboxamido, carbalkoxy, trifluoromethyl, hydroxyl, linear or branched —($C_1$-$C_6$)-alkyl, linear or branched —($C_2$-$C_6$)-alkenyl, halogen, —$OCF_3$, alkanoyloxy, alkanamido, alkanesulfonyl, alkanesulfonamido, phenyl, —$NR_{16}R_{17}$, -, —$COR_{16}$, —$OR_{16}$, —$SR_{16}$, —$OR_{16}$, or —$NO_2$, W, X, Y and Z are each independently —$CR_{18}R_{19}$—, —O—, —$NR_{18}$— or —S—;

X and Y are each independently —$CR_{18}R_{19}$—, —O—, —$NR_{18}$— or —S—;

$Z_1$ is carbon or nitrogen, $Z_2$ is carbon and $Z_3$ is carbon, nitrogen, oxygen or sulfur; wherein at least one of $Z_1$ and $Z_3$ is not carbon, wherein a double bond is optionally present between $Z_1$ and $Z_2$, wherein $A_1$ is attached to $R_7$ through $Z_1$, $Z_2$ or $Z_3$, except when $Z_3$ is oxygen, and further wherein when $R_7$ is linked to $Z_3$, then $Z_3$ is nitrogen;

$R_{12}$ and $R_{13}$ are each independently hydrogen or a linear or branched —($C_1$-$C_6$)-alkyl, wherein $R_{12}$ and $R_{13}$ may be attached at any of $Z_1$, $Z_2$ or $Z_3$, and further wherein $R_{13}$ is optionally present at $Z_1$ or $Z_2$ when $Z_3$ is oxygen;

$R_{14}$, $R_{15}$, $R_{16}$, $R_{17}$, $R_{18}$ and $R_{19}$ are each independently hydrogen, hydroxyl, halogen, a linear or branched ($C_1$-$C_6$)-alkyl or a linear or branched ($C_2$-$C_6$)-alkenyl; $R_{20}$ is a hydrogen, a linear or branched ($C_1$-$C_6$)-alkyl or a ($C_3$-$C_7$)-cycloalkyl; and the dotted lines represent optional double bonds.

This invention relates to both the R and S stereoisomers of the 3-amino-chroman or 2-amino-tetralin derivatives, as well as to racemic mixtures of the R and S stereoisomers. Throughout this application, the name of the product of this invention, where the absolute configuration of the 3-amino-chromans or 2-amino tetralins is not indicated, is intended to embrace the individual R and S enantiomers, as well as racemic mixtures.

This invention also relates to both the R and S stereoisomers at the carbon alpha or beta from the basic nitrogen. Throughout this application, the name of the product of this invention, where the absolute configuration at the above two positions is not indicated, is intended to embrace the individual R and S enantiomers.

Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 75%, and even more preferably less than about 90%. The preferred stereoisomer was isolated from racemic mixtures by high performance liquid chromatography (HPLC) using a chiral column.

The following compounds of Formula (I) are particularly preferred:

8-{[3-(5-fluoro-1H-indol-3-yl)propyl]amino}-2,3,8,9-tetrahydropyrano[3,2-e]isoindol-1(7H)-one;
(8S)-8-{[3-(5-fluoro-1H-indol-3-yl)propyl]amino}-2,3,8,9-tetrahydropyrano[3,2-e]isoindol-1(7H)-one;
(8R)-8-{[3-(5-fluoro-1H-indol-3-yl)propyl]amino}-2,3,8,9-tetrahydropyrano[3,2-e]isoindol-1(7H)-one;
8-{(cyclopropylmethyl)[3-(5-fluoro-1H-indol-3-yl)propyl]amino}-2,3,8,9-tetrahydropyrano[3,2-e]isoindol-1(7H)-one;
(8S)-8-{(cyclopropylmethyl)[3-(5-fluoro-1H-indol-3-yl)propyl]amino}-2,3,8,9-tetrahydropyrano[3,2-e]isoindol-1(7H)-one;
(8R)-8-{(cyclopropylmethyl)[3-(5-fluoro-1H-indol-3-yl)propyl]amino}-2,3,8,9-tetrahydropyrano[3,2-e]isoindol-1(7H)-one;
8-{cyclobutyl[3-(5-fluoro-1H-indol-3-yl)propyl]amino}-2,3,8,9-tetrahydropyrano[3,2-e]isoindol-1(7H)-one;
8-{(cyclobutylmethyl)[3-(5-fluoro-1H-indol-3-yl)propyl]amino}-2,3,8,9-tetrahydropyrano[3,2-e]isoindol-1(7H)-one;
8-{(cyclobutylmethyl)[3-(5-fluoro-1H-indol-3-yl)propyl]amino}-2,3,8,9-tetrahydropyrano[3,2-e]isoindol-1(7H)-one;
8-[[3-(5-fluoro-1H-indol-3-yl)propyl](methyl)amino]-2,3,8,9-tetrahydropyrano[3,2-e]isoindol-1(7H)-one;
8-{ethyl[3-(5-fluoro-1H-indol-3-yl)propyl]amino}-2,3,8,9-tetrahydropyrano[3,2-e]isoindol-1(7H)-one;
8-[[3-(5-fluoro-1H-indol-3-yl)propyl](isobutyl)amino]-2,3,8,9-tetrahydropyrano[3,2-e]isoindol-1(7H)-one;
8-{(cyclohexylmethyl)[3-(5-fluoro-1H-indol-3-yl)propyl]amino}-2,3,8,9-tetrahydropyrano[3,2-e]isoindol-1(7H)-one;
8-{benzyl[3-(5-fluoro-1H-indol-3-yl)propyl]amino}-2,3,8,9-tetrahydropyrano[3,2-e]isoindol-1(7H)-one;
8-[[3-(5-fluoro-1H-indol-3-yl)propyl](3-furylmethyl)amino]-2,3,8,9-tetrahydropyrano[3,2-e]isoindol-1(7H)-one;
8-{[3-(5,7-difluoro-1H-indol-3-yl)propyl]amino}-2,3,8,9-tetrahydropyrano[3,2-e]isoindol-1(7H)-one;
8-{(cyclobutyl[3-(5,7-difluoro-1H-indol-3-yl)propyl]amino}-2,3,8,9-tetrahydropyrano[3,2-e]isoindol-1(7H)-one;
3-{3-[(1-oxo-1,2,3,7,8,9-hexahydropyrano[3,2-e]isoindol-8-yl)amino]propyl}-1H-indole-5-carbonitrile;
3-{3-[(cyclopropylmethyl)(1-oxo-1,2,3,7,8,9-hexahydropyrano[3,2-e]isoindol-8-yl)amino]propyl}-1H-indole-5-carbonitrile;
3-(3-{(cyclopropylmethyl)[(8S)-1-oxo-1,2,3,7,8,9-hexahydropyrano[3,2-e]isoindol-8-yl]amino}propyl)-1H-indole-5-carbonitrile;
3-(3-{(cyclopropylmethyl)[(8R)-1-oxo-1,2,3,7,8,9-hexahydropyrano[3,2-e]isoindol-8-yl]amino}propyl)-1H-indole-5-carbonitrile;
8-{[4-(5-fluoro-1H-indol-3-yl)butyl]amino}-2,3,8,9-tetrahydropyrano[3,2-e]isoindol-1(7H)-one;
8-{(cyclopropylmethyl)[4-(5-fluoro-1H-indol-3-yl)butyl]amino}-2,3,8,9-tetrahydropyrano[3,2-e]isoindol-1(7H)-one;
8-{[(6-fluoro-2,3,4,9-tetrahydro-1H-carbazol-3-yl)methyl]amino}-2,3,8,9-tetrahydropyrano[3,2-e]isoindol-1(7H)-one;
8-{[3-(5-fluoro-1H-indol-3-yl)propyl]amino}-2-methyl-2,3,8,9-tetrahydropyrano[3,2-e]isoindol-1(7H)-one;
8-{(cyclopropylmethyl)[3-(5-fluoro-1H-indol-3-yl)propyl]amino}-2-methyl-2,3,8,9-tetrahydropyrano[3,2-e]isoindol-1(7H)-one;
(8S)-8-{(cyclopropylmethyl)[3-(5-fluoro-1H-indol-3-yl)propyl]amino}-2-methyl-2,3,8,9-tetrahydropyrano[3,2-e]isoindol-1(7H)-one;
(8R)-8-{(cyclopropylmethyl)[3-(5-fluoro-1H-indol-3-yl)propyl]amino}-2-methyl-2,3,8,9-tetrahydropyrano[3,2-e]isoindol-1(7H)-one;
8-[[3-(5-fluoro-1H-indol-3-yl)propyl](methyl)amino]-2-methyl-2,3,8,9-tetrahydropyrano[3,2-e]isoindol-1(7H)-one;
8-{ethyl[3-(5-fluoro-1H-indol-3-yl)propyl]amino}-2-methyl-2,3,8,9-tetrahydropyrano[3,2-e]isoindol-1(7H)-one;
8-[[3-(5-fluoro-1H-indol-3-yl)propyl](isobutyl)amino]-2-methyl-2,3,8,9-tetrahydropyrano[3,2-e]isoindol-1(7H)-one;
8-{cyclobutyl[3-(5-fluoro-1H-indol-3-yl)propyl]amino}-2-methyl-2,3,8,9-tetrahydropyrano[3,2-e]isoindol-1(7H)-one;
8-{(cyclobutylmethyl)[3-(5-fluoro-1H-indol-3-yl)propyl]amino}-2-methyl-2,3,8,9-tetrahydropyrano[3,2-e]isoindol-1(7H)-one;
3-{3-[(2-methyl-1-oxo-1,2,3,7,8,9-hexahydropyrano[3,2-e]isoindol-8-yl)amino]propyl}-1H-indole-5-carbonitrile;
3-{3-[(cyclopropylmethyl)(2-methyl-1-oxo-1,2,3,7,8,9-hexahydropyrano[3,2-e]isoindol-8-yl)amino]propyl}-1H-indole-5-carbonitrile;

8-{[3-(5,7-difluoro-1H-indol-3-yl)propyl]amino}-2-methyl-2,3,8,9-tetrahydropyrano[3,2-e]isoindol-1(7H)-one;
8-{(cyclopropylmethyl)[3-(5,7-difluoro-1H-indol-3-yl)propyl]amino}-2-methyl-2,3,8,9-tetrahydropyrano[3,2-e]isoindol-1(7H)-one;
8-{[(6-fluoro-2,3,4,9-tetrahydro-1H-carbazol-3-yl)methyl]amino}-2-methyl-2,3,8,9-tetrahydropyrano[3,2-e]isoindol-1(7H)-one;
8-{(cyclopropylmethyl)[(6-fluoro-2,3,4,9-tetrahydro-1H-carbazol-3-yl)methyl]amino}-2-methyl-2,3,8,9-tetrahydropyrano[3,2-e]isoindol-1(7H)-one;
8-{cyclobutyl[(6-fluoro-2,3,4,9-tetrahydro-1H-carbazol-3-yl)methyl]amino}-2-methyl-2,3,8,9-tetrahydropyrano[3,2-e]isoindol-1(7H)-one;
9-{[3-(5-fluoro-1H-indol-3-yl)propyl]amino}-3,4,9,10-tetrahydro-2H-pyrano[2,3-h]isoquinolin-1(8H)-one;
9-[[3-(5-fluoro-1H-indol-3-yl)propyl](methyl)amino]-3,4,9,10-tetrahydro-2H-pyrano[2,3-h]isoquinolin-1(8H)-one;
9-{ethyl[3-(5-fluoro-1H-indol-3-yl)propyl]amino}-3,4,9,10-tetrahydro-2H-pyrano[2,3-h]isoquinolin-1(8H)-one;
9-[[3-(5-fluoro-1H-indol-3-yl)propyl](propyl)amino]-3,4,9,10-tetrahydro-2H-pyrano[2,3-h]isoquinolin-1(8H)-one;
9-[[3-(5-fluoro-1H-indol-3-yl)propyl](isobutyl)amino]-3,4,9,10-tetrahydro-2H-pyrano[2,3-h]isoquinolin-1(8H)-one;
9-{(cyclopropylmethyl)[3-(5-fluoro-1H-indol-3-yl)propyl]amino}-3,4,9,10-tetrahydro-2H-pyrano[2,3-h]isoquinolin-1(8H)-one;
9-{cyclobutyl[3-(5-fluoro-1H-indol-3-yl)propyl]amino}-3,4,9,10-tetrahydro-2H-pyrano[2,3-h]isoquinolin-1(8H)-one;
9-[[3-(5-fluoro-1H-indol-3-yl)propyl](isopropyl)amino]-3,4,9,10-tetrahydro-2H-pyrano[2,3-h]isoquinolin-1(8H)-one;
9-{benzyl[3-(5-fluoro-1H-indol-3-yl)propyl]amino}-3,4,9,10-tetrahydro-2H-pyrano[2,3-h]isoquinolin-1(8H)-one;
9-[[3-(5-fluoro-1H-indol-3-yl)propyl](pyridin-4-ylmethyl)amino]-3,4,9,10-tetrahydro-2H-pyrano[2,3-h]isoquinolin-1(8H)-one;
9-[[3-(5-fluoro-1H-indol-3-yl)propyl](3,3,3-trifluoropropyl)amino]-3,4,9,10-tetrahydro-2H-pyrano[2,3-h]isoquinolin-1(8H)-one;
6-fluoro-9-{[3-(5-fluoro-1H-indol-3-yl)propyl]amino}-3,4,9,10-tetrahydro-2H-pyrano[2,3-h]isoquinolin-1(8H)-one;
9-{(cyclopropylmethyl)[3-(5-fluoro-1H-indol-3-yl)propyl]amino}-6-fluoro-3,4,9,10-tetrahydro-2H-pyrano[2,3-h]isoquinolin-1(8H)-one;
9-{ethyl[3-(5-fluoro-1H-indol-3-yl)propyl]amino}-6-fluoro-3,4,9,10-tetrahydro-2H-pyrano[2,3-h]isoquinolin-1(8H)-one;
8-{Cyclopropylmethyl-[3-(5-fluoro-3-methyl-2,3-dihydro-1H-indol-3-ylmethyl)-cyclobutyl]-amino}-5-methoxy-2,3,8,9-tetrahydro-7H-pyrano[3,2-e]isoindol-1-one;
8-{Cyclopropylmethyl-[3-(5-fluoro-3-methyl-2,3-dihydro-1H-indol-3-ylmethyl)-cyclobutyl]-amino}-5-fluoro-2,3,8,9-tetrahydro-7H-pyrano[3,2-e]isoindol-1-one;
8-{Cyclopbutylmethyl-[3-(5-fluoro-3-methyl-2,3-dihydro-1H-indol-3-ylmethyl)-cyclobutyl]-amino}-5-methoxy-2,3,8,9-tetrahydro-7H-pyrano[3,2-e]isoindol-1-one; or
8-{Cyclobutylmethyl-[3-(5-fluoro-3-methyl-2,3-dihydro-1H-indol-3-ylmethyl)-cyclobutyl]-amino}-5-fluoro-2,3,8,9-tetrahydro-7H-pyrano[3,2-e]isoindol-1-one.

The compound of general Formula (I) and compounds of structures (Ia) and (Ib) may be prepared by conventional synthetic techniques. In the following synthetic techniques, suitable aprotic polar solvents include, but are not limited to, dimethyl sulfoxide, dimethylformamide, tetrahydrofuran, acetone and ethanol. Suitable acid binding agents include, but are not limited to, organic tertiary bases, such as, for example, triethylamine, triethanolamine, 1,8-diazabicyclo[5.4.0]undec-7-ene (DBU), and diisopropylethylamine (DIPEA); and alkaline metal carbonates, such as, for example, potassium carbonate and sodium carbonates. Suitable reducing agents include, but are not limited to, sodium cyanoborohydride and sodium triacetoxyborohydride.

Methods for making cycloalkylfused indole, benzothiphene, benzofuran and indene derivatives are described in Provisional Application No. 60/653,666 (AM101783), filed Feb. 17, 2005. Methods for making 3-amino chroman and 2-amino tetralin derivatives are described in application Ser. No. 10/898,866, filed Jul. 26, 2004. The disclosures of methods for making these compounds are hereby incorporated by reference in their entirety.

General Synthetic Scheme(s) for Preparation of Compounds

Compounds of Formula (I) may be prepared by conventional methods as illustrated in the following synthetic schemes.

According to Scheme I, a suitably substituted ortho-bromobenzoic acid is protected as the methyl ester by alkylation with methyl iodide in the presence of a base such as DBU in a polar solvent like DMF. The bromo functionality is replaced by a methyl on treatment with dimethylzinc in the presence of a nickel catalyst. Benzylic bromination under standard conditions followed by heating with ammonia yields the lactam. Deprotection of the methyl ether under standard conditions with a Lewis acid such as BBr$_3$ yields the phenol. The phenol is propargylated under standard conditions with propargyl bromide and a base such as potassium carbonate. The propargyl ether is then subject to heating in N,N-diethylaniline to yield the dihydropyran.

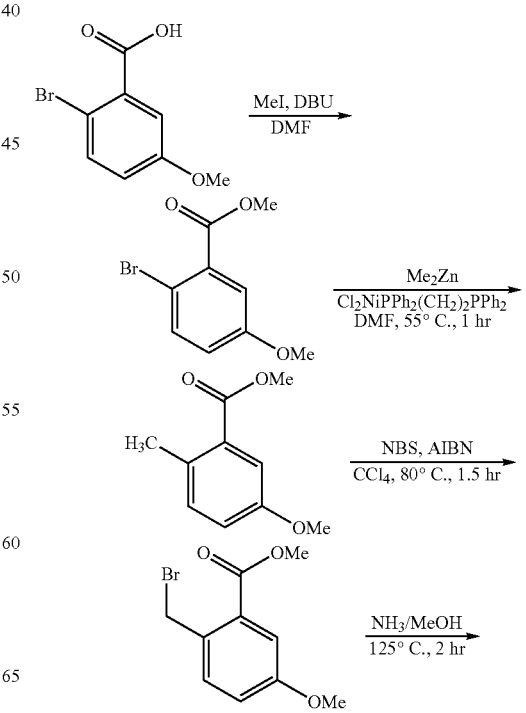

Scheme 1

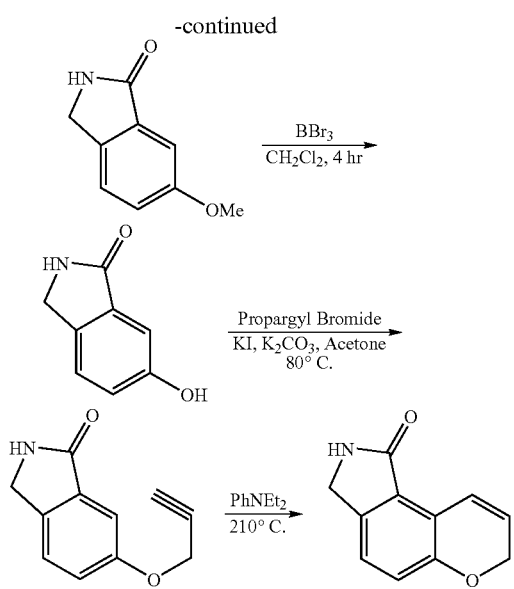

As shown in Scheme 2, the dihydropyran is subject to nitration with sodium nitrite and iodine. Reduction of the nitroolefin with sodium borohydride and silica yields the saturated nitro compound, which is reduced to the amine by treatment with Raney nickel and hydrazine.

This amine is then subject to reductive amination under standard conditions with a appropriately substituted aldehyde in the presence of sodiumcyanoborohydride and acetic acid in a polar solvent such as methanol. The groups $R_8$ and $R_{10}$ are as defined.

This secondary amine is then subject to one of two reaction conditions depending on the choice of $R_6$ that is required. When $R_6$ is a methyl, the secondary amine is alkylated with trimethyloxonium tetrafluoroborate in the presence of a base such as Hunig's base (diisopropylethylamine). For the rest, a second reductive amination gives additional compounds of this invention where $R_6$ is as defined in the generic structure. The preparation of the bicyclic aldehyde employed in this synthesis was previously disclosed in U.S. application Ser. No. 10/898,866, filed Jul. 26, 2004, which is hereby incorporated by reference in its entirety.

Scheme-2

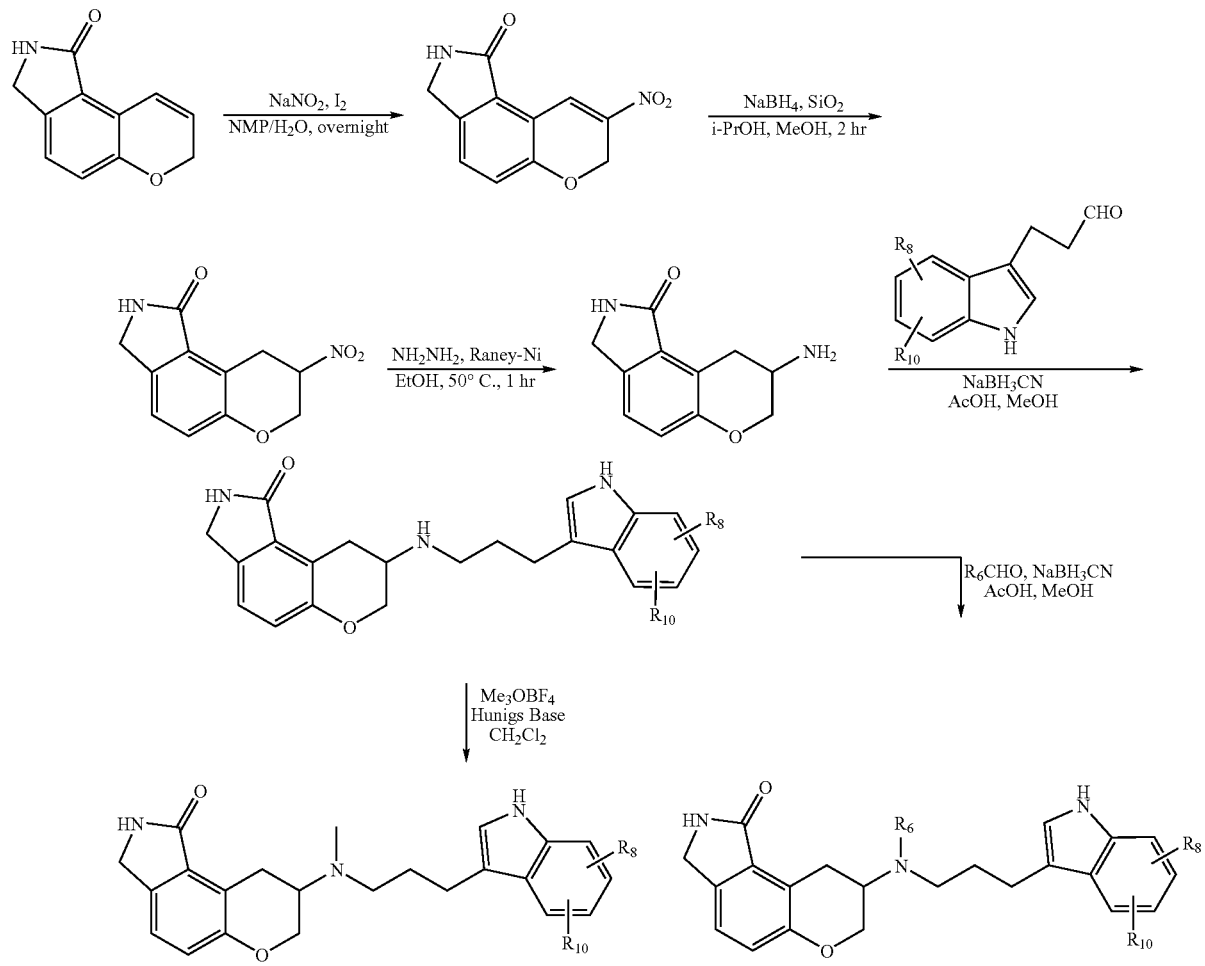

Compounds of this invention can also be prepared as in Scheme 3 by two successive reductive aminations. The preparation of the tricyclic aldehyde has been previously disclosed in Provisional Application No. 60/653,666 (AM101783), filed Feb. 17, 2005, which is hereby incorporated by reference in its entirety.

Scheme-3

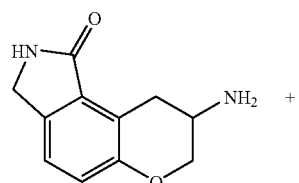

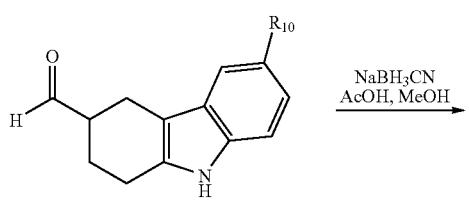

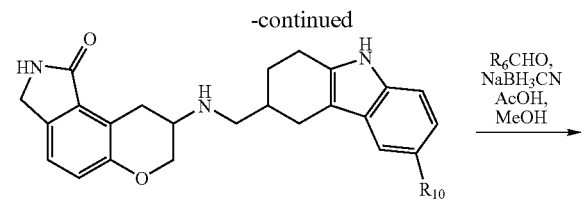

-continued

Scheme 4 describes the preparation of compounds in this invention wherein the nitrogen on the lactam moiety is alkylated. At the stage of the dihydropyran, which is prepared as described in Scheme 1, alkylation with an alkyl halide such as methyl iodide (MeI) after treatment with a base such as sodium hydride (NaH), yields the alkylated lactam. The rest of the synthesis follows the sequence described in Scheme 2.

Scheme-4

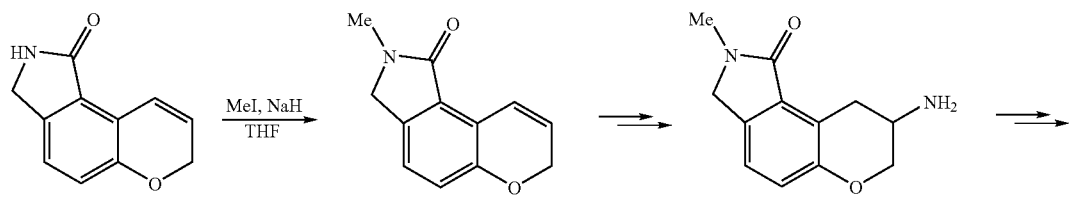

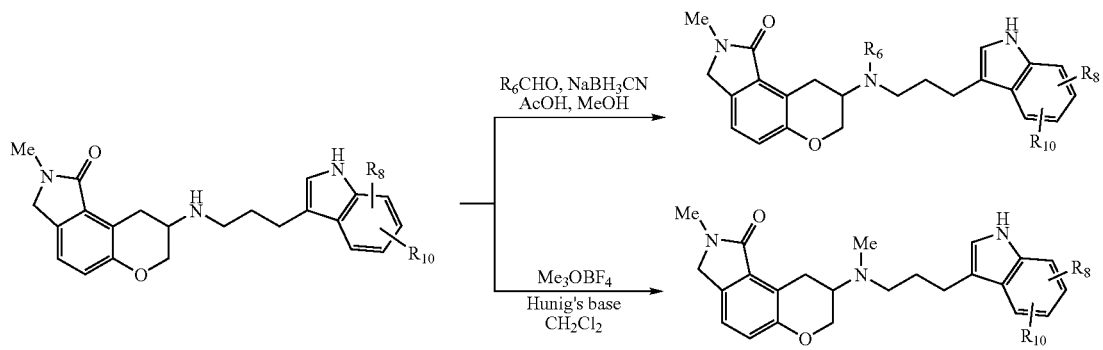

Scheme 5 describes the synthesis of compounds in this invention that contain a six-membered lactam ring. An appropriately substituted indanone is subject to a modified Schmidt rearrangement with sodium azide and methanesulfonic acid. This reaction yields a mixture of regioisomeric lactams from which the desired lactam is separated by standard column chromatography. This lactam is then subject to the same sequence of steps described in schemes 1 and 2 to yield the desired targets.

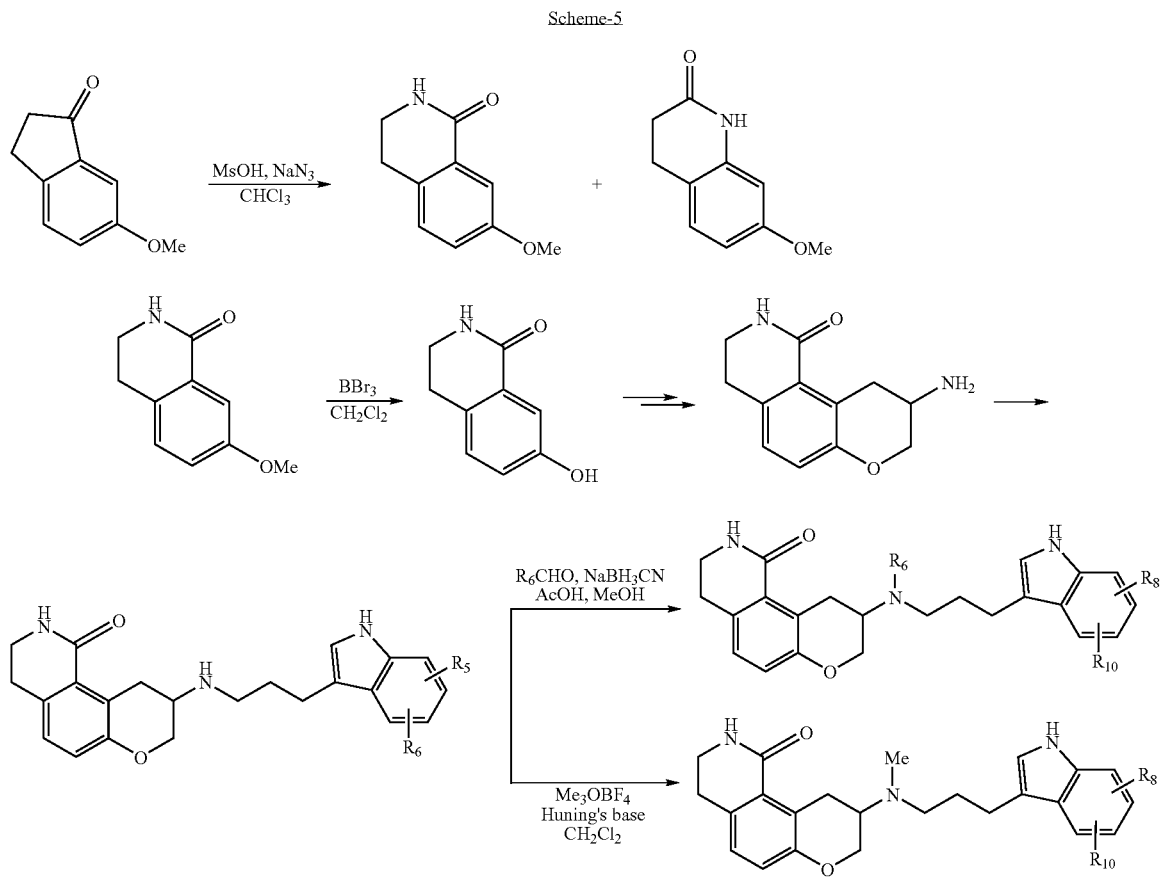

Scheme 6 describes the preparation of intermediates that contain a fluorine substituent para to the carbonyl group of the lactam. An appropriately substituted bromobenzene is subject to a Heck reaction with methyl acrylate in the presence of a catalytic amount of palladium acetate (Pd(OAc)$_2$) and tri-o-tolylphosphine (P(o-tol)$_3$). The unsaturated methyl ester is reduced to the saturated methyl ester under standard hydrogenation conditions using catalytic palladium on carbon under an atmosphere of hydrogen. The methyl ester is then hydrolysed under standard conditions to give the carboxylic acid. This carboxylic acid is then cyclized by heating in the presence of a Lewis acid such as aluminum trichloride (AlCl$_3$) to give the indanone. The indanone is then subject to a modified Schmidt rearrangement as described in scheme 5 to yield a mixture of regioisomeric lactams. The desired lactam (as shown) is then isolated by column chromatography.

This hydroxyl-lactam is then subject to the same sequence of steps shown in scheme 5 to yield compounds of this invention.

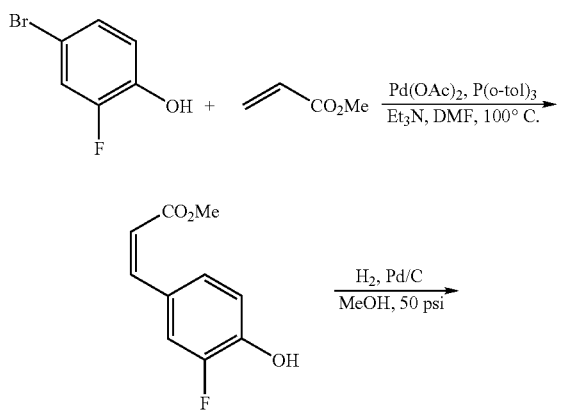

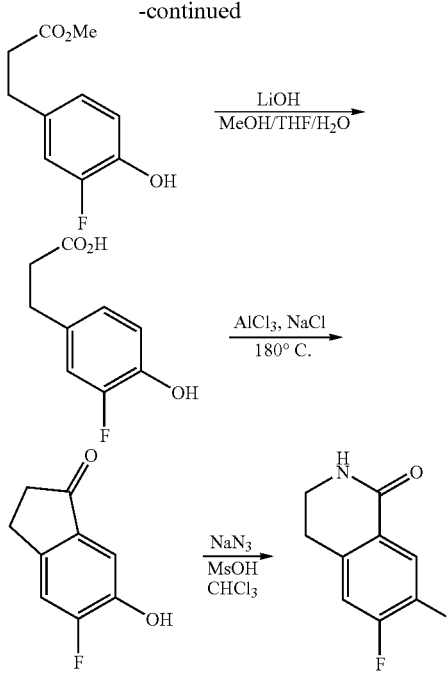

One of skill in the art will recognize that Schemes 1-6 can be adapted to produce the other compounds and pharmaceutically acceptable salts of compounds according to the present invention.

Therapeutic Administration

The terms "effective amount", "therapeutically effective amount" and "effective dosage" as used herein, refer to the amount of a compound of Formula (I), (Ia) and (Ib) that, when administered to a patient, is effective to at least partially ameliorate a condition form which the patient is suspected to suffer. Such conditions include, but are not limited to, depression (including, but not limited to major depressive disorder, childhood depression and dysthymia), anxiety, panic disorder, post-traumatic stress disorder, premenstrual dysphoric disorder (also known as premenstrual syndrome), attention deficit disorder (with or without hyperactivity), obsessive compulsive disorder, social anxiety disorder, generalized anxiety disorder, obesity, eating disorders such as anorexia nervosa and bulimia nervosa, vasomotor flushing, cocaine and alcohol addiction, sexual dysfunction, cognitive deficits resulting from neurodegenerative disorders like Alzheimer's disease, and related illnesses.

Compounds of Formula (I) have been found to act as serotonin reuptake inhibitors and to have an affinity for the 5-HT$_{1A}$ reuptake transporter. They are therefore useful in the treatment of diseases affected by disorders of the serotonin affected neurological systems, including, but not limited to, depression (including, but not limited to major depressive disorder, childhood depression and dysthymia), anxiety, panic disorder, post-traumatic stress disorder, premenstrual dysphoric disorder (also known as premenstrual syndrome), attention deficit disorder (with or without hyperactivity), obsessive compulsive disorder, social anxiety disorder, generalized anxiety disorder, obesity, eating disorders such as anorexia nervosa and bulimia nervosa, vasomotor flushing, cocaine and alcohol addiction, sexual dysfunction, cognitive deficits resulting from neurodegenerative disorders like Alzheimer's disease, and related illnesses. The present invention thus provides pharmaceutical compositions comprising at least one compound of Formula (I); and optionally one or more pharmaceutically acceptable carrier, excipient, or diluents.

When administered to an animal, the compounds or pharmaceutically acceptable salts of the compounds can be administered neat or as a component of a composition that comprises a physiologically acceptable carrier or vehicle. A composition of the invention can be prepared using a method comprising admixing the compound or a pharmaceutically acceptable salt of the compound and a physiologically acceptable carrier, excipient, or diluent. Admixing can be accomplished using methods well known for admixing a compound or a pharmaceutically acceptable salt of the compound and a physiologically acceptable carrier, excipient, or diluent.

The present compositions comprising compounds or pharmaceutically acceptable salts of the compounds of the invention can be administered orally. The compounds or pharmaceutically acceptable salts of compounds of the invention can also be administered by any other convenient route, for example, by infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result of release of the compound or a pharmaceutically acceptable salt of the compound into the bloodstream. The mode of administration is left to the discretion of the practitioner.

In one embodiment, the compound or a pharmaceutically acceptable salt of the compound is administered orally.

In another embodiment, the compound or a pharmaceutically acceptable salt of the compound is administered intravenously.

In another embodiment, it may be desirable to administer the compound or a pharmaceutically acceptable salt of the compound locally. This can be achieved, for example, by local infusion during surgery, topical application, e.g., in conjunction with a wound dressing after surgery, by injection, by means of a catheter, by means of a suppository or edema, or by means of an implant, said implant being of a porous, non-porous, or gelatinous material, including membranes, such as sialastic membranes, or fibers.

In certain embodiments, it can be desirable to introduce the compound or a pharmaceutically acceptable salt of the compound into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound or a pharmaceutically acceptable salt of the compound can be formulated as a suppository, with traditional binders and excipients such as triglycerides.

In another embodiment, the compound or a pharmaceutically acceptable salt of the compound can be delivered in a vesicle, in particular a liposome (see Langer, *Science* 249: 1527-1533 (1990) and Treat et al., *Liposomes in the Therapy of Infectious Disease and Cancer* 317-327 and 353-365 (1989)).

In yet another embodiment, the compound or a pharmaceutically acceptable salt of the compound can be delivered in a controlled-release system or sustained-release system (see, e.g., Goodson, in *Medical Applications of Controlled Release*, vol. 2, pp. 115-138 (1984)). Other controlled or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment, a controlled- or sustained-release system can be placed in proximity of a target of the compound or a pharmaceutically acceptable salt of the compound, e.g., the reproductive organs, thus requiring only a fraction of the systemic dose.

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to an animal. The physiologically acceptable excipient should be stable under the conditions of manufacture and storage and should be preserved against the contaminating action of microorganisms. Water is a particularly useful excipient when the compound or a pharmaceutically acceptable salt of the compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Liquid carriers may be used in preparing solutions, suspensions, emulsions, syrups, and elixirs. The compound or pharmaceutically acceptable salt of the compound of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and prenteral administration include water (particular containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable physiologically acceptable excipients are described in *Remington's Pharmaceutical Sciences* 1447-1676 (Alfonso R. Gennaro, ed., 19th ed. 1995).

In one embodiment, the compound or a pharmaceutically acceptable salt of the compound is formulated in accordance with routine procedures as a composition adapted for oral administration to humans. Compositions for oral delivery can be in the form of tablets, lozenges, buccal forms, troches, aqueous or oily suspensions or solutions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In powders, the carrier can be a finely divided solid, which is an admixture with the finely divided compound or pharmaceutically acceptable salt of the compound. In tablets, the compound or pharmaceutically acceptable salt of the compound is mixed with a carrier having the necessary compression properties in suitable proportions and compacted in the shape and size desired. The powders and tablets can contain up to about 99% of the compound or pharmaceutically acceptable salt of the compound.

Capsules may contain mixtures of the compounds or pharmaceutically acceptable salts of the compounds with inert fillers and/or diluents such as pharmaceutically acceptable starches (e.g., corn, potato, or tapioca starch), sugars, artificial sweetening agents, powdered celluloses (such as crystalline and microcrystalline celluloses), flours, gelatins, gums, etc.

Tablet formulations can be made by conventional compression, wet granulation, or dry granulation methods and utilize pharmaceutically acceptable diluents, binding agents, lubricants, disintegrants, surface modifying agents (including surfactants), suspending or stabilizing agents (including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrroldine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Moreover, when in a tablet or pill form, the compositions can be coated to delay disintegration and absorption in the gastrointestinal tract, thereby providing a sustained action over an extended period of time. Selectively permeable membranes surrounding an osmotically active driving compound or a pharmaceutically acceptable salt of the compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment, the compound or a pharmaceutically acceptable salt of the compound can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the compound or a pharmaceutically acceptable salt of the compound is to be administered by infusion, it can be dispensed, for example, with an infusion bottle containing sterile pharmaceutical grade water or saline. Where the compound or a pharmaceutically acceptable salt of the compound is administered by injection, an ampule of sterile water for injection or saline can be provided so that the ingredients can be mixed prior to administration.

In another embodiment, the compound or pharmaceutically acceptable salt of the compound can be administered transdermally through the use of a transdermal patch. Transdermal administrations include administrations across the surface of the body and the inner linings of the bodily passages including epithelial and mucosal tissues. Such administrations can be carried out using the present compounds or pharmaceutically acceptable salts of the compounds, in lotions, creams, foams, patches, suspensions, solutions, and suppositories (e.g., rectal or vaginal).

Transdermal administration can be accomplished through the use of a transdermal patch containing the compound or pharmaceutically acceptable salt of the compound and a carrier that is inert to the compound or pharmaceutically acceptable salt of the compound, is non-toxic to the skin, and allows delivery of the agent for systemic absorption into the blood stream via the skin. The carrier may take any number of forms such as creams or ointments, pastes, gels, or occlusive devices. The creams or ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the compound or pharmaceutically acceptable salt of the compound into the blood stream, such as a semi-permeable membrane covering a reservoir containing the compound or pharmaceutically acceptable salt of the compound with or without a carrier, or a matrix containing the active ingredient.

The compounds or pharmaceutically acceptable salts of the compounds of the invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

The compound or a pharmaceutically acceptable salt of the compound can be administered by controlled-release or sustained-release means or by delivery devices that are known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of the compound or a pharmaceutically acceptable salt of the compound to treat or prevent a condition related to or affected by the reuptake of serotonin and the 5-$HT_{1A}$ receptor in a minimal amount of time. Advantages of controlled- or sustained-release compositions include extended activity of the drug, reduced dosage frequency, and increased compliance by the animal being treated. In addition, controlled- or sustained-release compositions can favorably affect the time of onset of action or other characteristics, such as blood levels of the compound or a pharmaceutically acceptable salt of the compound, and can thus reduce the occurrence of adverse side effects.

Controlled- or sustained-release compositions can initially release an amount of the compound or a pharmaceutically acceptable salt of the compound that promptly produces the desired therapeutic or prophylactic effect, and gradually and continually release other amounts of the compound or a pharmaceutically acceptable salt of the compound to maintain this level of therapeutic or prophylactic effect over an extended period of time. To maintain a constant level of the compound or a pharmaceutically acceptable salt of the compound in the body, the compound or a pharmaceutically acceptable salt of the compound can be released from the dosage form at a rate that will replace the amount of the compound or a pharmaceutically acceptable salt of the compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In certain embodiments, the present invention is directed to prodrugs of the compounds or pharmaceutically acceptable salts of compounds of the present invention. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); "*Design and*

*Application of Prodrugs"*, *Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Delivery Systems*, American Chemical Society (1975).

The amount of the compound or a pharmaceutically acceptable salt of the compound that is effective for treating or preventing a condition related to or affected by the reuptake of serotonin and the 5-HT$_{1A}$ receptor will vary. In vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound or a pharmaceutically acceptable salt of the compound is administered, the effective dosage amounts correspond to the total amount administered.

The amount of the compound or a pharmaceutically acceptable salt of the compound that is effective for treating or preventing a condition related to or affected by the reuptake of serotonin and the 5-HT$_{1A}$ receptor will typically range from about 0.001 mg/kg to about 250 mg/kg of body weight per day, in one embodiment, from about 1 mg/kg to about 250 mg/kg body weight per day, in another embodiment, from about 1 mg/kg to about 50 mg/kg body weight per day, and in another embodiment, from about 5 mg/kg to about 25 mg/kg of body weight per day. The compounds may be given in a single dose or in two or more divided doses.

In one embodiment, the pharmaceutical composition is in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from 0.1 to 100 mg of a compound of the invention and preferably from 2 to 50 mg. Still further preferred unit dosage forms contain 5 to 25 mg of a compound of the present invention. Such compositions may be administered from 1 to 6 times a day, more usually from 1 to 4 times a day.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient. Effective administration of the compounds of this invention may be given at an oral dose of from about 0.1 mg/day to about 1000 mg/day. Preferably, administration will be from about 10 mg/day to about 600 mg/day, more preferably, a starting dose is about 5 mg/day with gradual increase in the daily dose to about 150 mg/day, to provide the desired dosage level in the human. Doses may be administered in a single dose or in two or more divided doses. The projected daily dosages are expected to vary with route of administration.

The compound or a pharmaceutically acceptable salt of the compound can be assayed in vitro or in vivo for the desired therapeutic or prophylactic activity prior to use in humans. Animal model systems can be used to demonstrate safety and efficacy.

The present methods for treating or preventing a condition related to or affected by the reuptake of serotonin and the 5-HT$_{1A}$ receptor can further comprise administering another therapeutic agent to the animal being administered the compound or a pharmaceutically acceptable salt of the compound. In one embodiment, the other therapeutic agent is administered in an effective amount.

Effective amounts of the other therapeutic agents are well known to those skilled in the art. However, it is well within the skilled artisan's purview to determine the other therapeutic agent's optimal effective amount range. The compound or a pharmaceutically acceptable salt of the compound and the other therapeutic agent can act additively or synergistically.

In one embodiment, the compound or a pharmaceutically acceptable salt of the compound is administered concurrently with another therapeutic agent.

In one embodiment, a composition comprising an effective amount of the compound or a pharmaceutically acceptable salt of the compound and an effective amount of another therapeutic agent within the same composition can be administered.

In another embodiment, a composition comprising an effective amount of the compound or a pharmaceutically acceptable salt of the compound and a separate composition comprising an effective amount of another therapeutic agent can be concurrently administered. In another embodiment, an effective amount of the compound or a pharmaceutically acceptable salt of the compound is administered prior to or subsequent to administration of an effective amount of another therapeutic agent. In this embodiment, the compound or a pharmaceutically acceptable salt of the compound is administered while the other therapeutic agent exerts its therapeutic effect, or the other therapeutic agent is administered while the compound or a pharmaceutically acceptable salt of the compound exerts its preventative or therapeutic effect for treating or preventing a condition related to or affected by the reuptake of serotonin and the 5-HT$_{1A}$ receptor.

Thus, in one embodiment, the invention provides a composition comprising an effective amount of the compound or a pharmaceutically acceptable salt of the compound of the present invention and a pharmaceutically acceptable carrier. In another embodiment, the pharmaceutically acceptable carrier is suitable for oral administration and the composition comprises an oral dosage form.

(c) Therapeutic or Prophylactic Uses

In one embodiment, the compounds or pharmaceutically acceptable salts of the compounds of the present invention are useful as serotonin reuptake inhibitors and as 5-HT$_{1A}$ receptor agonists or antagonists. Accordingly, the compounds and pharmaceutically acceptable salts of the compounds of the present invention are useful for treating a mammal with a condition related to or affected by the reuptake of serotonin and the 5-HT$_{1A}$ receptor.

In one embodiment, the invention provides a method for treating a condition related to or affected by the reuptake of serotonin and the 5-HT$_{1A}$ receptor, comprising administering to a mammal in need thereof a compound or a pharmaceutically acceptable salt of the compound of Formula (I), Formula (Ia) or Formula (Ib) or Formula (Ic) in an amount effective to treat a condition related to or affected by the reuptake of serotonin and the 5-HT$_{1A}$ receptor.

In one embodiment, the condition is depression (including, but not limited to major depressive disorder, childhood depression and dysthymia). In additional embodiments, the condition is anxiety, panic disorder or post-traumatic stress disorder.

In a further embodiment, the condition is premenstrual dysphoric disorder (also known as premenstrual syndrome).

Additionally, the condition to be treated or prevented can be attention deficit disorder (with or without hyperactivity).

A further embodiment is the treatment or prevention of obsessive compulsive disorder. Additionally, the condition to be treated or prevented is social anxiety disorder or generalized anxiety disorder.

In one embodiment, the condition to be treated or prevented is obesity, eating disorders such as anorexia nervosa and bulimia nervosa, vasomotor flushing, cocaine and alcohol addiction or sexual dysfunction.

Further conditions to be treated or prevented are cognitive deficits resulting from neurodegenerative disorders like Alzheimer's disease, and related illnesses in mammals including man.

In one embodiment, the present invention is directed to a method for modulating the reuptake of serotonin or the activity of a 5-HT$_{1A}$ receptor, comprising contacting the receptor with an effective amount of a compound or pharmaceutically acceptable salt of the compound of Formula (I) or Formula (Ia). In one embodiment, the method further comprises determining the activity of the receptor. In one embodiment, the step of determining the activity of the receptor is performed before the step of contacting the receptor with the compound or a pharmaceutically acceptable salt of the compound. In another embodiment, the step of determining the activity of the receptor is performed after the step of contacting the receptor with the compound or a pharmaceutically acceptable salt of the compound.

The compounds and pharmaceutically acceptable salts of the compounds of Formula (I) or Formula (Ia) or Formula (Ib) or Formula (Ic) are also useful in the manufacture of medicaments for treating a condition related to or affected by the reuptake of serotonin and the 5-HT$_{1A}$ receptor in a mammal.

Accordingly, in one embodiment, the invention provides the use of a compound or pharmaceutically acceptable salt of the compound of Formula (I) or Formula (Ia) or Formula (Ib) or Formula (Ic) for the manufacture of a medicament for treating a condition related to or affected by the reuptake of serotonin and the 5-HT$_{1A}$ receptor.

In one embodiment, the present invention is directed to the use of a compound or pharmaceutically acceptable salt of the compound of Formula (I) or Formula (Ia) or Formula (Ib) or Formula (Ic) for the manufacture of a medicament for modulating the activity of reuptake of serotonin and of the 5-HT$_{1A}$ receptor. In one embodiment, the medicament is also for determining the activity of the receptor.

The present invention further provides a compound of the invention for use as an active therapeutic substance. Compounds of the invention are of particular use in the treatment of diseases affected by disorders of serotonin.

The present invention further provides a method for treating depression (including, but not limited to major depressive disorder, childhood depression and dysthymia), anxiety, panic disorder, post-traumatic stress disorder, premenstrual dysphoric disorder (also known as premenstrual syndrome), attention deficit disorder (with or without hyperactivity), obsessive compulsive disorder, social anxiety disorder, generalized anxiety disorder, obesity, eating disorders such as anorexia nervosa and bulimia nervosa, vasomotor flushing, cocaine and alcohol addiction, sexual dysfunction, cognitive deficits resulting from neurodegenerative disorders like Alzheimer's disease, and related illnesses in mammals including man, which comprises administering to the afflicted mammal an effective amount of a compound or a pharmaceutical composition of the invention.

EXAMPLES

Example 1

8-{[3-(5-fluoro-1H-indol-3-yl)propyl]amino}-2,3,8,9-tetrahydropyrano[3,2-e]isoindol-1(7H)-one (3)

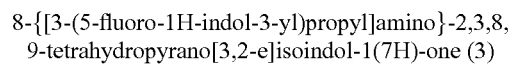

To a solution of 8-amino-2,3,8,9-tetrahydropyrano[3,2-e]isoindol-1(7H)-one (1) (200 mg, 0.98 mmol) in anhydrous MeOH (20 ml) was added 3-(5-fluoro-1H-indol-3-yl) propanal (2) (191 mg, 1 mmol), AcOH (0.14 ml), and NaBH$_3$CN (123 mg, 1.96 mmol). Resulting reaction mixture was stirred at room temperature for 2 hr. The solvent was removed in vacuo and the residue was re-dissolved in CH$_2$Cl$_2$ (150 ml). The solution was washed with 1 N NaOH (20 ml) and H$_2$O, Sat. NaCl. The organic solution was separated, dried over Na$_2$SO$_4$, then concentrated in vacuo. The crude compound was purified on silica gel eluting with EtOAc/Hexane (4:1) to yield (3) (304 mg, 82%) as a white solid. MS (APPI) m/z 380.

Example 2

(8S)-8-{[3-(5-fluoro-1H-indol-3-yl)propyl]amino}-2,3,8,9-tetrahydropyrano[3,2-e]isoindol-1(7H)-one (4)

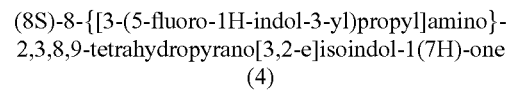

The title compound (4) was chirally separated from (3) from Example 1. It was dissolved methylene chloride and treated with 1 equivalent of etherate HCl to give HCl salt. [a]D25=−11.0° (c=1% SOLUTION, DMSO); MS (ES) m/z 380.1.

Example 3

(8R)-8-{[3-(5-fluoro-1H-indol-3-yl)propyl]amino}-2,3,8,9-tetrahydropyrano[3,2-e]isoindol-1(7H)-one (5)

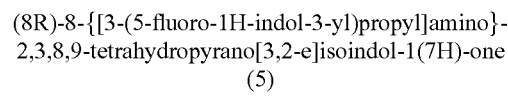

The title compound (5) was chirally separated from (3) from Example 1. It was dissolved in methylene chloride and treated with 1 equivalent of etherate HCl to give HCl salt. [a]D25=+12.6° (c=1% SOLUTION, DMSO); MS (ES) m/z 380.1.

Example 4

8-{(cyclopropylmethyl)[3-(5-fluoro-1H-indol-3-yl)propyl]amino}-2,3,8,9-tetrahydropyrano[3,2-e]isoindol-1(7H)-one (6)

To a solution of (7) WAY-255377 (45 mg, 0.12 mmol) in anhydrous methanol (3 ml) was added cyclopropanecarboxaldehyde (21 mg, 0.30 mmol), acetic acid (0.017 ml), and NaBH$_3$CN (15 mg, 0.24 mmol). Resulting reaction mixture was stirred at room temperature for 4 hr. The solvent was removed in vacuo and the residue was re-dissolved in CH$_2$Cl$_2$ (150 ml). The solution was washed with 1 N NaOH and H$_2$O, Sat. NaCl. The organic solution was separated, dried over Na$_2$SO$_4$, then concentrated in vacuo. The crude compound was purified on silica gel eluting with EtOAc/Hexane (2:1) to yield free tertiary amine, which was treated with 1 equivalent of etherate HCl to give HCl salt (41 mg, 73%). MS (ES) m/z 432.2.

Example 5

(8S)-8-{(cyclopropylmethyl)[3-(5-fluoro-1H-indol-3-yl)propyl]amino}-2,3,8,9-tetrahydropyrano[3,2-e]isoindol-1(7H)-one (8)

The title compound (8) was chirally separated from (6) in Example 4. It was dissolved in methylene chloride and treated with 1 equivalent of etherate HCl to give HCl salt. [a]D25=+18.0° (c=4.93 MG/0.7 ML, DMSO); MS (ES) m/z 434.2.

Example 6

(8R)-8-{(cyclopropylmethyl)[3-(5-fluoro-1H-indol-3-yl)propyl]amino}-2,3,8,9-tetrahydropyrano[3,2-e]isoindol-1(7H)-one (9)

The title compound (9) was chirally separated from (6) in Example 4. It was dissolved in methylene chloride and treated with 1 equivalent of etherate HCl to give HCl salt. [a]D25=−22.70° (c=5.86/0.7 ML, DMSO); MS (ES) m/z 434.2.

Example 7

8-{cyclobutyl[3-(5-fluoro-1H-indol-3-yl)propyl]amino}-2,3,8,9-tetrahydropyrano[3,2-e]isoindol-1(7H)-one (10)

The title compound (10) was prepared as in Example 4. MS (ES) m/z 434.2.

Example 8

8-{(cyclobutylmethyl)[3-(5-fluoro-1H-indol-3-yl)propyl]amino}-2,3,8,9-tetrahydropyrano[3,2-e]isoindol-1(7H)-one (11)

The title compound (11) was prepared as in Example 4. MS (ES) m/z 446.2

Example 9

8-[[3-(5-fluoro-1H-indol-3-yl)propyl](methyl)amino]-2,3,8,9-tetrahydropyrano[3,2-e]isoindol-1(7H)-one (12)

To a mixture of (3) (52 mg, 0.137 mmol) and Me$_3$OBF$_4$ (40 mg, 0.274 mmol) in methylene chloride (5 ml) was added Hunig's base (40 μl, 0.274 mmol). The reaction mixture was stirred at 50° C. for 2 hr, then diluted with 100 ml of methylene chloride. It was washed with H$_2$O, saturated NaCl. The organic solution was dried over Na2SO4 and concentrated in vacuo. The residue was purified on silica gel eluting with (80% EtOAc/Hexane) to give the title compound, which was treated with 1 equivalent of etherate HCl to give HCl salt. MS (ES) m/z 394.1.

Example 10

8-{ethyl[3-(5-fluoro-1H-indol-3-yl)propyl]amino}-2,3,8,9-tetrahydropyrano[3,2-e]isoindol-1(7H)-one (13)

The title compound (13) was prepared as in Example 4. MS (ES) m/z 408.2.

Example 11

8-[[3-(5-fluoro-1H-indol-3-yl)propyl](isobutyl)amino]-2,3,8,9-tetrahydropyrano[3,2-e]isoindol-1(7H)-one (14)

The title compound (14) was prepared as in Example 4. MS (ES) m/z 436.3.

Example 12

8-{(cyclohexylmethyl)[3-(5-fluoro-1H-indol-3-yl)propyl]amino}-2,3,8,9-tetrahydropyrano[3,2-e]isoindol-1(7H)-one (15)

The title compound (15) was prepared as Example 4. MS (ES) m/z 476.3.

Example 13

8-{benzyl[3-(5-fluoro-1H-indol-3-yl)propyl]amino}-2,3,8,9-tetrahydropyrano[3,2-e]isoindol-1(7H)-one (16)

The title compound (16) was prepared as in Example 4. MS (ES) m/z 470.2.

Example 14

8-[[3-(5-fluoro-1H-indol-3-yl)propyl](3-furylmethyl)amino]-2,3,8,9-tetrahydropyrano[3,2-e]isoindol-1(7H)-one (17)

The title compound (17) was prepared as in Example 4. MS (ES) m/z 460.2.

Example 15

8-{[3-(5,7-difluoro-1H-indol-3-yl)propyl]amino}-2,3,8,9-tetrahydropyrano[3,2-e]isoindol-1(7H)-one (18)

The title compound (18) was prepared as in Example 1. MS (ES) m/z 398.1.

Example 16

8-{cyclobutyl[3-(5,7-difluoro-1H-indol-3-yl)propyl]amino}-2,3,8,9-tetrahydropyrano[3,2-e]isoindol-1(7H)-one (19)

The title compound (19) was prepared as in Example 4. MS (ES) m/z 450.2.

Example 17

3-{3-[(1-oxo-1,2,3,7,8,9-hexahydropyrano[3,2-e]isoindol-8-yl)amino]propyl}-1H-indole-5-carbonitrile (20)

To a mixture of (1) (60 mg, 0.294 mmol), 4-(5-fluoro-1H-indol-3-yl)butanal (21), 64 mg, 0.309 mmol) in acetic acid (37 µl, 0.62 mmol) and methanol (2 ml) was added NaBH$_3$CN (37 mg, 0.59 mmol) in portions. Resulting mixture was stirred for 1.5 hr. The solvent was removed in vacuo and the residue was dissolved in CH$_2$Cl$_2$ and washed with 1 N NaOH and saturated NaCl. The organic solution was dried over Na$_2$SO$_4$ and concentrated in vacuo. The compound was purified on silica gel eluting with 60% EtOAc/Hexane to give (20) as a solid (78 mg, 69%). The title compound was dissolved in methylene chloride and treated with 1 equivalent of etherate HCl to give HCl salt. MS (ES) m/z 385.2.

Example 18

3-{3-[(cyclopropylmethyl)(1-oxo-1,2,3,7,8,9-hexahydropyrano[3,2-e]isoindol-8-yl)amino]propyl}-1H-indole-5-carbonitrile (22)

The title compound (22) was prepared as in Example 4. MS (ES) m/z 441.2.

Example 19

3-(3-{(cyclopropylmethyl)[(8S)-1-oxo-1,2,3,7,8,9-hexahydropyrano[3,2-e]isoindol-8-yl]amino}propyl)-1H-indole-5-carbonitrile (23)

The title compound (23) was chirally separated from Example 18. It was dissolved in methylene chloride and treated with 1 equivalent of etherate HCl to give HCl salt. [a]D25=+23.06° (c=5.04 MG/0.7 ML, DMSO); MS (ES) m/z 441.2.

Example 20

3-(3-{(cyclopropylmethyl)[(8R)-1-oxo-1,2,3,7,8,9-hexahydropyrano[3,2-e]isoindol-8-yl]amino}propyl)-1H-indole-5-carbonitrile (24)

The title compound (24) was chirally separated from Example 18. It was dissolved in methylene chloride and treated with 1 equivalent of etherate HCl to give HCl salt. [a]D25=−24.30° (c=5.24 MG/0.7 ML, DMSO); MS m/z 441.2.

Example 21

8-{[4-(5-fluoro-1H-indol-3-yl)butyl]amino}-2,3,8,9-tetrahydropyrano[3,2-e]isoindol-1(7H)-one (25)

To a mixture of (1) (60 mg, 0.294 mmol), 4-(5-fluoro-1H-indol-3-yl)butanal (21), 63 mg, 0.294 mmol) in acetic acid (37 µl, 0.62 mmol) and methanol (4 ml) was added NaBH$_3$CN (37 mg, 0.588 mmol) in portions. Resulting mixture was stirred for 1.5 hr. The solvent was removed in vacuo and the residue was dissolved in CH$_2$Cl$_2$ and washed with 1 N NaOH and saturated NaCl. The organic solution was dried over Na$_2$SO$_4$ and concentrated in vacuo. The compound was purified on silica gel eluting with 60% EtOAc/Hexane to give (25) as a solid (90 mg, 78%). MS (ES) m/z 394.2;

Example 22

8-{(cyclopropylmethyl)[4-(5-fluoro-1H-indol-3-yl)butyl]amino}-2,3,8,9-tetrahydropyrano[3,2-e]isoindol-1(7H)-one (26)

The title compound (26) was prepared as in Example 4. MS (ES) m/z 448.2

Example 23

8-{[(6-fluoro-2,3,4,9-tetrahydro-1H-carbazol-3-yl)methyl]amino}-2,3,8,9-tetrahydropyrano[3,2-e]isoindol-1(7H)-one (27)

To a mixture of (1) (60 mg, 0.294 mmol), 6-fluoro-2,3,4,9-tetrahydro-1H-carbazole-3-carbaldehyde ((28), 64 mg, 0.294 mmol) in acetic acid (38 mg, 0.588 mmol) and methanol (3 ml) was added NaBH$_3$CN (37 mg, 0.588 mmol) in portions. The resulting mixture was stirred for 40 min. The solvent was removed in vacuo and the residue was dissolved in methylene chloride. The organic solution was washed with 1N NaOH and saturated NaCl before being dried over with Na$_2$SO$_4$. The concentration of organic solution in vacuo gave crude (27), which was purified on silica gel eluting with 80% EtOAc/Hexane to give a white solid (71 mg, 60%). MS (ES) m/z 406.2

Example 24

8-{[3-(5-fluoro-1H-indol-3-yl)propyl]amino}-2-methyl-2,3,8,9-tetrahydropyrano[3,2-e]isoindol-1(7H)-one (29)

To a mixture of (30) (90 mg, 0.41 mmol), 3-(5-fluoro-1H-indol-3-yl)propanal ((2), 93 mg, 0.580 mmol) in acetic acid (49 µl, 0.588 mmol) and methanol (8 ml) was added NaBH$_3$CN (52 mg, 0.82 mmol) in portions. The resulting mixture was stirred for 45 min. The solvent was removed in vacuo and the residue was dissolved in methylene chloride. The organic solution was washed with 1N NaOH and saturated NaCl before being dried over with Na$_2$SO$_4$. Concentration of organic solution gave the crude compound, which was purified on silica gel (80% EtOAc/Hexane) to give (29) as a free base. It was treated with 1 equivalent etherate HCl to give the title compound as a HCl salt. MS (ES) m/z 394.2.

Example 25

8-{(cyclopropylmethyl)[3-(5-fluoro-1H-indol-3-yl)propyl]amino}-2-methyl-2,3,8,9-tetrahydropyrano[3,2-e]isoindol-1(7H)-one (30)

The title compound (30) was prepared as in Example 4. MS (ES) m/z 448.3.

Example 26

(8S)-8-{(cyclopropylmethyl)[3-(5-fluoro-1H-indol-3-yl)propyl]amino}-2-methyl-2,3,8,9-tetrahydropyrano[3,2-e]isoindol-1(7H)-one (31)

The title compound (31) was chirally separated from (30). It was dissolved methylene chloride and treated with 1 equivalent of etherate HCl to give HCl salt. [a]D25=+16.69° (c=4.53/0.7 ML, DMSO); MS (ES) m/z 448.2.

Example 27

(8R)-8-{(cyclopropylmethyl)[3-(5-fluoro-1H-indol-3-yl)propyl]amino}-2-methyl-2,3,8,9-tetrahydropyrano[3,2-e]isoindol-1(7H)-one (32)

The title compound (32) was chirally separated from (30). It was dissolved methylene chloride and treated with 1 equivalent of etherate HCl to give HCl salt. [a]D25=−14.66° (c=4.01 MG/0.7 ML, DMSO); MS (ES) m/z 448.2.

Example 28

8-[[3-(5-fluoro-1H-indol-3-yl)propyl](methyl)amino]-2-methyl-2,3,8,9-tetrahydropyrano[3,2-e]isoindol-1(7H)-one (33)

The title compound (33) was prepared as in Example 9. MS (ES) m/z 408.2.

Example 29

8-{ethyl[3-(5-fluoro-1H-indol-3-yl)propyl]amino}-2-methyl-2,3,8,9-tetrahydropyrano[3,2-e]isoindol-1(7H)-one (34)

The title compound (34) was prepared as in Example 4. MS (ES) m/z 422.2.

Example 30

8-[[3-(5-fluoro-1H-indol-3-yl)propyl](isobutyl)amino]-2-methyl-2,3,8,9-tetrahydropyrano[3,2-e]isoindol-1(7H)-one (35)

The title compound (35) was prepared as in Example 4. MS (ES) m/z 448.2.

Example 31

8-{cyclobutyl[3-(5-fluoro-1H-indol-3-yl)propyl]amino}-2-methyl-2,3,8,9-tetrahydropyrano[3,2-e]isoindol-1(7H)-one (36)

The title compound (36) was prepared as in Example 4. MS (ES) m/z 446.2.

Example 32

8-{(cyclobutylmethyl)[3-(5-fluoro-1H-indol-3-yl)propyl]amino}-2-methyl-2,3,8,9-tetrahydropyrano[3,2-e]isoindol-1(7H)-one (37)

The title compound (37) was prepared as in Example 4. MS (ES) m/z 460.2.

Example 33

3-{3-[(2-methyl-1-oxo-1,2,3,7,8,9-hexahydropyrano[3,2-e]isoindol-8-yl)amino]propyl}-1H-indole-5-carbonitrile (38)

The title compound (38) was prepared as in Example 17. MS (ES) m/z 399.2;

Example 34

3-{3-[(cyclopropylmethyl)(2-methyl-1-oxo-1,2,3,7,8,9-hexahydropyrano[3,2-e]isoindol-8-yl)amino]propyl}-1H-indole-5-carbonitrile (39)

The title compound (39) was prepared as in Example 4. MS (ES) m/z 455.3.

Example 35

8-{[3-(5,7-difluoro-1H-indol-3-yl)propyl]amino}-2-methyl-2,3,8,9-tetrahydropyrano[3,2-e]isoindol-1(7H)-one (40)

To a mixture of (1) (202 mg, 0.99 mmol), 3-(5,7-difluoro-1H-indol-3-yl)propanal ((41), 247 mg, 1.09 mmol) in acetic acid (145 μl, 2.36 mmol) and methanol (10 ml) was added NaBH$_3$CN (126 mg, 2.00 mmol) in portions. Resulting mixture was stirred for 2.0 hr. The solvent was removed in vacuo and the residue was dissolved in CH$_2$Cl$_2$ and washed with 1 N NaOH and saturated NaCl. The organic solution was dried over Na$_2$SO$_4$ and concentrated in vacuo. The compound was purified on silica gel eluting with 70% EtOAc/Hexane to give (18), which was treated with 1 equivalent of etherate HCl to form HCl salt. MS (ES) m/z 412.2.

Example 36

8-{(cyclopropylmethyl)[3-(5,7-difluoro-1H-indol-3-yl)propyl]amino}-2-methyl-2,3,8,9-tetrahydropyrano[3,2-e]isoindol-1(7H)-one (41)

The title compound (41) was prepared as in Example 4. MS (ES) m/z 466.2.

Example 37

8-{[(6-fluoro-2,3,4,9-tetrahydro-1H-carbazol-3-yl)methyl]amino}-2-methyl-2,3,8,9-tetrahydropyrano[3,2-e]isoindol-1(7H)-one (42)

The title compound (42) was prepared as in Example 4. MS (ES) m/z 420.2.

Example 38

8-{(cyclopropylmethyl)[(6-fluoro-2,3,4,9-tetrahydro-1H-carbazol-3-yl)methyl]amino}-2-methyl-2,3,8,9-tetrahydropyrano[3,2-e]isoindol-1(7H)-one (43)

To a solution of (42) (52 mg, 0.124 mmol) in anhydrous methanol (5 ml) was added cyclopropanecarboxaldehyde (10 mg, 0.149 mmol), acetic acid (0.015 ml), and NaBH$_3$CN (15 mg, 0.24 mmol). Resulting reaction mixture was stirred at room temperature for 4 hr. The solvent was removed in vacuo and the residue was re-dissolved in CH$_2$Cl$_2$ (150 ml). The solution was washed with 1 N NaOH, H$_2$O and saturated NaCl. The organic solution was separated, dried over Na₂SO₄, then concentrated in vacuo. The crude compound was purified on silica gel eluting with EtOAc/Hexane (2:1) to yield free tertiary amine, which was treated with 1 equivalent of etherate HCl to give HCl salt. MS (ES) m/z 473.3.

Example 39

8-{cyclobutyl[(6-fluoro-2,3,4,9-tetrahydro-1H-carbazol-3-yl)methyl]amino}-2-methyl-2,3,8,9-tetrahydropyrano[3,2-e]isoindol-1(7H)-one (44)

The title compound (44) was prepared as in Example 4. MS (ES) m/z 472.3.

Example 40

9-{[3-(5-fluoro-1H-indol-3-yl)propyl]amino}-3,4,9,10-tetrahydro-2H-pyrano[2,3-h]isoquinolin-1(8H)-one (45)

To a mixture of 9-amino-3,4,9,10-tetrahydro-2H-pyrano[2,3-h]isoquinolin-1(8H)-one (46) (130 mg, 0.596 mmol), 3-(5-fluoro-1H-indol-3-yl)propanal ((2), 113 mg, 0.596 mmol) in acetic acid (70 μl) and methanol (20 ml) was added NaBH₃CN (75 mg, 1.19 mmol) in portions. The resulting mixture was stirred for 2 hr. The solvent was removed in vacuo and the residue was dissolved in methylene chloride. The organic solution was washed with 1N NaOH and saturated NaCl before being dried over with Na₂SO₄. Concentration of organic solution gave the crude compound, which was purified on silica gel (100% EtOAc) to give the desired compound, which was treated with 1 equivalent of etherate HCL to form HCl salt for title compound. MS (APPI) m/z 394.4.

Example 41

9-[[3-(5-fluoro-1H-indol-3-yl)propyl](methyl)amino]-3,4,9,10-tetrahydro-2H-pyrano[2,3-h]isoquinolin-1(8H)-one (47)

The title compound (47) was prepared as in Example 9. MS (ES) m/z 406.0.

Example 42

9-{ethyl[3-(5-fluoro-1H-indol-3-yl)propyl]amino}-3,4,9,10-tetrahydro-2H-pyrano[2,3-h]isoquinolin-1(8H)-one (48)

To a solution of 9-amino-6-fluoro-3,4,9,10-tetrahydro-2H-pyrano[2,3-h]isoquinolin-1(8H)-one (49) (55 mg, 0.14 mmol) in anhydrous methanol (3 ml) was added acetoaldehyde (12 mg, 0.21 mmol), acetic acid (0.018 ml), and NaBH₃CN (18 mg, 0.29 mmol). Resulting reaction mixture was stirred at room temperature for 3 hr. The solvent was removed in vacuo and the residue was re-dissolved in CH₂Cl₂ (150 ml). The solution was washed with 1 N NaOH and H₂O, Sat. NaCl. The organic solution was separated, dried over Na₂SO₄, and then concentrated in vacuo. The crude compound was purified on silica gel eluting with EtOAc/Hexane (2:1) to yield free tertiary amine, which was treated with 1 equivalent of etherate HCl to give HCl salt (35 mg, 60%). S (APPI) m/z 422.

Example 43

9-[[3-(5-fluoro-1H-indol-3-yl)propyl](propyl)amino]-3,4,9,10-tetrahydro-2H-pyrano[2,3-h]isoquinolin-1(8H)-one (50)

The title compound (50) was prepared as in Example 42. MS (ES) m/z 436.2.

Example 44

9-[[3-(5-fluoro-1H-indol-3-yl)propyl](isobutyl)amino]-3,4,9,10-tetrahydro-2H-pyrano[2,3-h]isoquinolin-1(8H)-one (51)

The title compound (51) was prepared as in Example 42. MS (ES) m/z 450.2.

Example 45

9-{(cyclopropylmethyl)[3-(5-fluoro-1H-indol-3-yl)propyl]amino}-3,4,9,10-tetrahydro-2H-pyrano[2,3-h]isoquinolin-1(8H)-one (52)

The title compound (52) was prepared as in Example 42. MS (ES) m/z 448.2.

Example 46

9-{cyclobutyl[3-(5-fluoro-1H-indol-3-yl)propyl]amino}-3,4,9,10-tetrahydro-2H-pyrano[2,3-h]isoquinolin-1(8H)-one (53)

The title compound (53) was prepared as in Example 42. MS (ES) m/z 448.2.

Example 47

9-[[3-(5-fluoro-1H-indol-3-yl)propyl](isopropyl)amino]-3,4,9,10-tetrahydro-2H-pyrano[2,3-h]isoquinolin-1(8H)-one (54)

The title compound (54) was prepared as in Example 42. MS (ES) m/z 434.2.

Example 48

9-{benzyl[3-(5-fluoro-1H-indol-3-yl)propyl]amino}-3,4,9,10-tetrahydro-2H-pyrano[2,3-h]isoquinolin-1(8H)-one (55)

The title compound (55) was prepared as in Example 42. MS (ES) m/z 482.2;

Example 49

9-[[3-(5-fluoro-1H-indol-3-yl)propyl](pyridin-4-ylmethyl)amino]-3,4,9,10-tetrahydro-2H-pyrano[2,3-h]isoquinolin-1(8H)-one (56)

The title compound (56) was prepared as Example 42. MS (ES) m/z 483.2.

Example 50

9-[[3-(5-fluoro-1H-indol-3-yl)propyl](3,3,3-trifluoropropyl)amino]-3,4,9,10-tetrahydro-2H-pyrano[2,3-h]isoquinolin-1(8H)-one (57)

The title compound (57) was prepared as in Example 42. MS (ES) m/z 490.2;

Example 51

6-fluoro-9-{[3-(5-fluoro-1H-indol-3-yl)propyl] amino}-3,4,9,10-tetrahydro-2H-pyrano[2,3-h]iso-quinolin-1(8H)-one (58)

To a solution of 9-amino-6-fluoro-3,4,9,10-tetrahydro-2H-pyrano[2,3-h]isoquinolin-1(8H)-one (49) (110 mg, 0.47 mmol) in anhydrous methanol (7 ml) was added 3-(5-fluoro-1H-indol-3-yl) propanal (2) (89 mg, 0.47 mmol), acetic acid (0.060 ml), and $NaBH_3CN$ (59 mg, 0.930 mmol). Resulting reaction mixture was stirred at room temperature for 3 hr. The solvent was removed in vacuo and the residue was re-dissolved in $CH_2Cl_2$ (120 ml). The solution was washed with 1 N NaOH and $H_2O$, saturated. NaCl. The organic solution was separated, dried over $Na_2SO_4$, then concentrated in vacuo. The crude compound was purified on silica gel eluting with 80% EtOAc/Hexane to yield the title compound. MS (ES) m/z 410.2.

Example 52

9-{(cyclopropylmethyl)[3-(5-fluoro-1H-indol-3-yl) propyl]amino}-6-fluoro-3,4,9,10-tetrahydro-2H-pyrano[2,3-h]isoquinolin-1(8H)-one (59)

To a solution of (58) (55 mg, 0.134 mmol) in anhydrous methanol (4 ml) was added cyclopropanecarboxaldehyde (12 mg, 0.161 mmol), acetic acid (20 µl), and $NaBH_3CN$ (17 mg, 0.268 mmol). Resulting reaction mixture was stirred at room temperature for 2 hr. The solvent was removed in vacuo and the residue was re-dissolved in $CH_2Cl_2$ (120 ml). The solution was washed with 1 N NaOH and $H_2O$, saturated NaCl. The organic solution was separated, dried over $Na_2SO_4$, then concentrated in vacuo. The crude compound was purified on silica gel eluting with 80% EtOAc/Hexane to yield free tertiary amine, which was treated with 1 equivalent of etherate HCl to give HCl salt (41 mg, 60%). MS (APPI) m/z 466.

Example 53

9-{ethyl[3-(5-fluoro-1H-indol-3-yl)propyl]amino}-6-fluoro-3,4,9,10-tetrahydro-2H-pyrano[2,3-h]iso-quinolin-1(8H)-one (60)

The title compound (60) was prepared as in Example 52. MS (APPI) m/z 440.

Example 54

3-{3-[(6-fluoro-1-oxo-1,3,4,8,9,10-hexahydro-2H-pyrano[2,3-h]isoquinolin-9-yl)amino]propyl}-1H-indole-5-carbonitrile (61)

The title compound (61) was prepared as in Example 17. MS (ES) m/z 419.1.

Example 55

3-{3-[ethyl(6-fluoro-1-oxo-1,3,4,8,9,10-hexahydro-2H-pyrano[2,3-h]isoquinolin-9-yl)amino]propyl}-1H-indole-5-carbonitrile (62)

The title compound (62) was prepared as in Example 4. MS (ES) m/z 445.2.

Example 56

3-{3-[(cyclopropylmethyl)(6-fluoro-1-oxo-1,3,4,8,9, 10-hexahydro-2H-pyrano[2,3-h]isoquinolin-9-yl) amino]propyl}-1H-indole-5-carbonitrile (63)

The title compound (63) was prepared as in Example 4. MS (ES) m/z 471.2.

Example 57

3-{3-[cyclobutyl(6-fluoro-1-oxo-1,3,4,8,9,10-hexahydro-2H-pyrano[2,3-h]isoquinolin-9-yl)amino] propyl}-1H-indole-5-carbonitrile (64)

The title compound (64) was prepared as in Example 4. MS (ES) m/z 471.2.

Example 58

3-{3-[(6-fluoro-1-oxo-1,3,4,8,9,10-hexahydro-2H-pyrano[2,3-h]isoquinolin-9-yl)(propyl)amino]pro-pyl}-1H-indole-5-carbonitrile (65)

The title compound (65) was prepared as in Example 4. MS (ES) m/z 459.2.

Example 59

3-{3-[(6-fluoro-1-oxo-1,3,4,8,9,10-hexahydro-2H-pyrano[2,3-h]isoquinolin-9-yl)(isobutyl)amino]pro-pyl}-1H-indole-5-carbonitrile (66)

The title compound (66) was prepared as in Example 4. MS (ES) m/z 473.1.

Example 60

3-{3-[(6-fluoro-1-oxo-1,3,4,8,9,10-hexahydro-2H-pyrano[2,3-h]isoquinolin-9-yl)(isopropyl)amino] propyl}-1H-indole-5-carbonitrile (67)

The title compound (67) was prepared as in Example 4. MS (APPI) m/z 461.

Example 61

3-{3-[benzyl(6-fluoro-1-oxo-1,3,4,8,9,10-hexahydro-2H-pyrano[2,3-h]isoquinolin-9-yl)amino]pro-pyl}-1H-indole-5-carbonitrile (68)

The title compound (68) was prepared as in Example 4. MS (APPI) m/z 509.

Example 62

8-amino-2,3,8,9-tetrahydropyrano[3,2-e]isoindol-1 (7H)-one (1)

To a solution of 8-nitro-2,3,8,9-tetrahydropyrano[3,2-e] isoindol-1(7H)-one ((69), 700 mg, 2.99 mmol) in EtOH (35 ml)/THF (5 ml) was added hydrazine monohydrate (1.65 ml, 34 mmol), followed by addition of Raney-Nickel (50 mg). The reaction mixture was stirred for 4 hr. The catalyst residue was filtered under vacuum and organic solution was concentrated in vacuo to give the title compound as a solid (420 mg, 69%). MS (ES) m/z 205.1

Example 63

8-nitro-2,3,8,9-tetrahydropyrano[3,2-e]isoindol-1(7H)-one (69)

To 8-nitro-2,3-dihydropyrano[3,2-e]isoindol-1(7H)-one ((70), 1.1 g, 4.74 mmol) in solvent A ($CHCl_3$, 100 ml) and solvent B (i-PrOH 4 ml) was added silica gel (3.3 g), followed by addition of sodium boronhydride (400 mg, 11.5 mmol) in portions. Resulting mixture was stirred for 2 hr. The silica gel was filtered and washed well with $CHCl_3$. The filtrate was washed with $H_2O$, and sat NaCl. The organic solution was separated and dried over $Na_2SO_4$ and concentrated in vacuo to give the title compound (790 mg, 71%) as a solid.
MS (APPI) m/z 235.2.

Example 64

8-nitro-2,3-dihydropyrano[3,2-e]isoindol-1(7H)-one (70)

To a mixture of 2,3-dihydropyrano[3,2-e]isoindol-1(7H)-one ((71) 2.3 g, 12.3 mmol) in N-methylpyrrolidine (150 ml) and $H_2O$ (3 ml) was added $NaNO_2$ (3.4 g, 49.2 mmol) in portions. To the mixture cooled at 0° C. was added iodine (9.4 g, 36.9 mmol). The reaction mixture was stirred for 3 hr, then quenched with 58% $NaHSO_3$ (12 ml), $H_2O$ (12 ml), followed by addition of another 30 ml of 58% $NaHSO_3$ solution. The solid was participated, filtered, and washed with $H_2O$. The desired compound was air-dried under vacuum to give the title compound (2.41 g, 84%) as a yellow solid. MS (ES) m/z 233.2.

Example 65

2,3-dihydropyrano[3,2-e]isoindol-1(7H)-one (71)

The mixture of 6-(prop-2-ynyloxy)isoindolin-1-one ((72), 4.4 g, 23.5 mmol) and N,N-Diethylaniline 70 ml) was stirred at 210° C. for overnight. Reaction solution was directly loaded on silica gel eluting with Hexane/EtOAc/$CH_2Cl_2$ (3:3:1 ratio) to give the title compound (2.8 g, 64%) as a brown solid. MS (ES) m/z 188.1.

Example 66

6-(prop-2-ynyloxy)isoindolin-1-one (72)

The mixture of 6-hydroxyisoindolin-1-one ((73), 5.1 g, 34.2 mmol), propargyl bromide (80% solution in toluene, 5.70 ml, 51.3 mmol) $K_2CO_3$ (9.44 g, 68.4 mmol), KI (1.14 g, 6.8 mmol) in acetone was refluxed for overnight. The reaction mixture was filtered under vacuum and concentrated in vacuo to give the title compound (4.4 g, 68%) as a solid. MS (ES) m/z 188.1.

Example 67

6-hydroxyisoindolin-1-one (73)

To a suspension of (74) (7.07 g, 43.4 mmol) in $CH_2Cl_2$ (600 ml) was added $BBr_3$ (1M in $CH_2Cl_2$, 86.7 ml). The reaction mixture was stirred at room temperature for 4 hr. The solvent and boron residue was removed in vacuo and the remaining solid was dissolved in $CH_2Cl_2$, the solution was neutralized with 1 N NaOH (PH=6.5). Desired compound was precipitated out and filtered. The organic solution was separated and washed with sat. NaCl, dried over $Na_2SO_4$ to give the title compound (combined weight 5.1 g, 78%). MS (ES) m/z 150.1.

Example 68

6-methoxyisoindolin-1-one (74)

A solution of methyl 2-(bromomethyl)-5-methoxybenzoate ((75), 5.0 g, 19.3 mmol) in MeOH was placed in pressure flask and to it ammonia/methanol (2M, 30 ml) was added. Resulting mixture was stirred at 125° C. for 2 hr. The solvent and excess $NH_3$ was removed in vacuo and the residue was triturated with Hexane/EtOAc (1:2 ratio). The compound was filtered under vacuum and air-dried for 2 hr to give the title compound (2.51 g, 65%) as a pale yellow solid. The filtrated was concentrated and purified on silica gel (Hexane/EtOAc/MeOH 3:1:0.5 ratio) to yield another 270 mg of desired compound. Combined yield was 86%. MS (ES) m/z 164.1.

Example 69

Methyl 2-(bromomethyl)-5-methoxybenzoate (75)

A mixture of (5.68 g, 31.1 mmol), NBS (6.74 g, 37.9 mmol), AIBN (259 mg, 1.58 mmol) in carbon tetrachloride was refluxed for 2 hr. The reaction mixture was cooled at room temperature and the solid was filtrated under vacuum. The filtrate was concentrated in vacuo to obtain (75) (8.01 g, >98%) as an oil without purification.

Example 70

8-amino-2-methyl-2,3,8,9-tetrahydropyrano[3,2-e]isoindol-1(7H)-one (31)

The title compound (31) was prepared as in Example 62. MS (ES) m/z 219.2.

Example 71

2-methyl-8-nitro-2,3,8,9-tetrahydropyrano[3,2-e]isoindol-1(7H)-one (76)

The title compound (76) was prepared as in Example 63. MS (ES) m/z 249.1.

Example 72

2-methyl-8-nitro-2,3-dihydropyrano[3,2-e]isoindol-1(7H)-one (77)

The title compound (77) was prepared as in Example 64. MS (ES) m/z 247.0.

Example 73

2-methyl-2,3-dihydropyrano[3,2-e]isoindol-1(7H)-one (78)

To a suspension of 2,3-dihydropyrano[3,2-e]isoindol-1(7H)-one ((71), 100 mg, 0.54 mmol) in THF (5 ml) was added sodium hydride (95%, 21 mg, 0.80 mmol) in portions. Resulting mixture was stirred for 45 min, then added iodomethane (0.37 ml) via syringe. Reaction was continued for 2.5 hr before removing THF in vacuo. The residue was dissolved in $CH_2Cl_2$, washed with $H_2O$, sat. NaCl. The organic solution was dried over anhydrous $Na_2SO_4$ and concentrated in vacuo to give WAY 257034 as a solid (88 mg, 74%). MS (ES) m/z 202.1.

Example 74

9-amino-3,4,9,10-tetrahydro-2H-pyrano[2,3-h]isoquinolin-1(8H)-one (46)

The title compound (46) was prepared as in Example 62. MS (ES) m/z 219.1.

Example 75

9-nitro-3,4,9,10-tetrahydro-2H-pyrano[2,3-h]isoquinolin-1(8H)-one (79)

The title compound (79) was prepared as in Example 63. MS (ES) m/z 249.1.

Example 76

9-nitro-3,4-dihydro-2H-pyrano[2,3-h]isoquinolin-1(8H)-one (80)

The title compound (80) was prepared as in Example 64. MS (ES) m/z 247.1.

Example 77

3,4-dihydro-2H-pyrano[2,3-h]isoquinolin-1(8H)-one (81)

The title compound (81) was prepared as in Example 65. MS (ES) m/z 202.1.

Example 78

7-(prop-2-yn-1-yloxy)-3,4-dihydroisoquinolin-1(2H)-one (82)

The title compound (82) was prepared as in Example 66. MS (ES) m/z 202.1.

Example 79

7-hydroxy-3,4-dihydroisoquinolin-1(2H)-one (83)

The title compound (83) was prepared as in Example 67. MS (ES) m/z 162.1.

Example 80

7-methoxy-3,4-dihydroisoquinolin-1(2H)-one (84)

To a mixture of 6-Methoxy-1-indanone (15 g, 92.6 mmol), sodium azide (26.7 g, 277.8 mmol), in $CHCl_3$ was added methane sulfonic acid (60 g, 926 mmol) via addition funnel at 0° C. Reaction mixture was warm to room temperature. Stirring was continued for 3 hr, then poured into cold water. The organics were extracted with methylene chloride and washed with water, sat. NaCl and dried over $Na_2SO_4$. Organic solution was concentrated in vacuo and the residue was purified with silica gel eluting with 20% EtOAc/Hexane to give the title compound as a yellow solid (10.5 g, 63%). MS (ES) m/z 178.1.

Example 81

9-amino-6-fluoro-3,4,9,10-tetrahydro-2H-pyrano[2,3-h]isoquinolin-1(8H)-one (49)

The title compound (49) was prepared as in Example 62. MS (ES) m/z 237.1.

Example 82

6-fluoro-9-nitro-3,4,9,10-tetrahydro-2H-pyrano[2,3-h]isoquinolin-1(8H)-one (85)

The title compound (85) was prepared as in Example 63. MS (ES) m/z 267.1.

Example 83

6-fluoro-9-nitro-3,4-dihydro-2H-pyrano[2,3-h]isoquinolin-1(8H)-one (86)

The title compound (86) was prepared as in Example 64. MS (ES) m/z 265.1.

Example 84

6-fluoro-3,4-dihydro-2H-pyrano[2,3-h]isoquinolin-1(8H)-one (87)

The title compound (87) was prepared as in Example 65. MS (ES) m/z 220.1.

Example 85

6-fluoro-7-(prop-2-yn-1-yloxy)-3,4-dihydroisoquinolin-1(2H)-one (88)

The title compound (88) was prepared as in Example 66. MS (ES) m/z 220.1.

Example 86

6-fluoro-7-hydroxy-3,4-dihydroisoquinolin-1(2H)-one (89)

To a solution of 5-fluoro-6-hydroxyindan-1-one ((90), 10.5 g, 63.3 mmol) in chloroform (600 ml) was added $NaN_3$ (12.3 g, 190 mmol), followed by dropwise addition of methanasulfonic acid (33 ml, 506 mmol). Resulting mixture was stirred for 3 hr. The reaction mixture was poured into cold water and extracted with chloroform (3×). Organic extracts were combined and washed with $H_2O$ and sat. NaCl, then dried over $Na_2SO_4$. Concentration in vacuo gave a mixture of required product and reversed lactam. Purification of crude product on silica eluting with 30-60% EtOAc/Hexane offered the title compound as a off-white solid (5.3 g, 46%). MS (ES) m/z 180.0.

Example 87

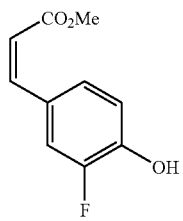

Methyl(2E)-3-(3-Fluoro-4-hydroxyphenyl)acrylate (91)

To a mixture of 4-Bromo-2-fluorophenol (25 g, 0.13 mol) and methyl acrylate (23.41 ml, 0.26 mol) in DMF (500 ml) was added triethylamine (36 ml, 0.26 mol) and tri-o-tolylphosphine (1.95 g, 6.5 mmol) and Pd(OAc)$_2$ (2.91 g, 13 mmol). Reaction mixture was stirred under nitrogen at 100° C. for 3 hr. About 200 ml of DMF was removed by rotavapor and remaining reaction solution was diluted with EtOAc (300 ml). Palladium residue was filtered under vacuum and the filtrate was washed H$_2$O and sat. NaCl. Organic solution was dried over Na$_2$SO$_4$ and concentrated in vacuo. The compound was purified with chromatograghy eluting with EtOAc/Hex (20-40%) to give WAY-263609 as a solid (18.2 g, 72%). $^1$H NMR/CDCl$_3$, δ, 7.60 (d, 1H), 7.19-7.30 (m, 2H), 6.97-7.04 (t, 1H), 6.30 (d, 1H), 5.90 (s, 1H), 3.80 (s, 3H).

Example 88

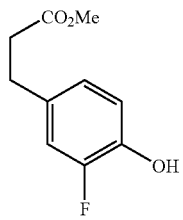

Methyl(2E)-3-(3-Fluoro-4-hydroxyphenyl)propanoate (92)

A mixture of (91) (18.2 g, 93.3 mmol) Pd/C (1.9 g) in MeOH (150 ml) was hydrogenated at 50 psi for 18 hr. The reaction mixture was filtered and the filtrate was concentrated in vacuo to give WAY 263610 as a solid (15.4 g, 84%). $^1$H NMR/CDCl$_3$, δ, 6.85(m, 2H), 6.80 (d, 1H), 4.20-4.50 (broad s, 1H), 3.67 (s, 3H), 2.81-2.88 (t, 3H), 2.55-2.60 (t, 2H).

Example 89

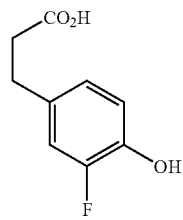

3-(3-fluoro-4-hydroxyphenyl)propanoic acid (93)

To a solution of (92) (15 g, 75.8 mmol) in MeOH (150 ml)/THF (150 ml)/H$_2$O (50 ml) was added LiOH (6.36 g, 103 mmol). The reaction mixture was stirred for 3 hr. The solvents were removed in vacuo and to the residue was added CH$_2$Cl$_2$ (500 ml). It was acedified with 2N HCl until PH=2. Organic solution was separated, washed with sat. NaCl and dried over Na$_2$SO$_4$. Concentration in vacuo gave WAY-263667 (11.6 g, 83%). $^1$H NMR/CDCl$_3$, δ, 6.80-6.95 (m, 3H), 2.84-2.90 (t, 2H), 2.60-2.66 (t, 2H). MS (ES) m/z 183.0.

Example 90

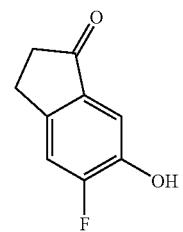

5-fluoro-6-hydroxyindan-1-one (90)

A mixture of (93) (11.6 g, 63.0 mmol) and AlCl$_3$ (57 g, 87.6 mmol), NaCl (25 g, 483 mmol) was melted and stirred at 185° C. for 15 min, then poured into cold water. The suspended solid was stirred for 10 min before being filtered. The solid was air-dried for 4 hr under vacuum to give 263709 as an off-white solid (9.2 g, 88%). $^1$H NMR/CD$_3$OD, δ, 7.21 (d, 1H), 7.18 (d, 1H), 3.02-3.08 (t, 2H), 2.61-2.68 (t, 3H). MS (ES) m/z 165.1.

Example 91

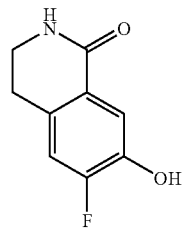

6-fluoro-7-hydroxy-3,4-dihydroisoquinolin-1(2H)-one (89)

To a solution of (90) (10.5 g, 63.3 mmol) in chloroform (600 ml) was added NaN$_3$ (12.3 g, 190 mmol), followed by dropwise addition of methanasulfonic acid (33 ml, 506 mmol). Resulting mixture was stirred for 3 hr. The reaction mixture was poured into cold water and extracted with chloroform (3×). Organic extracts were combined and washed with H$_2$O and sat. NaCl, then dried over Na$_2$SO$_4$. Concentration in vacuo gave a mixture of required product and reversed lactam. Purification of crude product on silica eluting with 30-60% EtOAc/Hex offered WAY-263746 as a off-white solid (5.3 g, 46%). $^1$H NMR/CD$_3$OD, δ, 7.48 (d, 1H), 7.00 (d, 1H), 3.43-3.49 (t, 2H), 2.83-2.89 (t, 2H). MS (ES) m/z 180.0.

Example 92

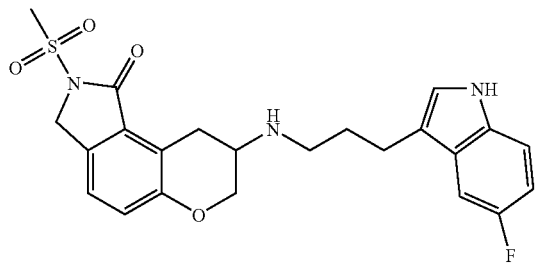

8-{[3-(5-fluoro-1H-indol-3-yl)propyl]amino}-2-(methylsulfonyl)-2,3,8,9-tetrahydropyrano[3,2-e]isoindol-1(7H)-one (94)

To a solution of methylsulfonyl substituted lactam amino chroman (118 mg, 0.418 mol) and 3-(5-fluoro-1H-indol-3-yl)propanal (88 mg, 0.460 mmol) in methanol (15 ml) was added acetic acid (0.05 ml), followed by addition of NaBH$_3$CN (53 mg, 0.836 mmol). Reaction mixture was stirred at room temperature for 2 hr. The solvent was removed in vacuo and the residue was partitioned in methylene chloride and H$_2$O. The organic solution was washed with sat. NaCl, dried over Na$_2$SO$_4$ and concentrated in vacuo. The residue was purified on silica gel eluting with 80% EtOAc/Hexane to give the title compound (94) (25 mg). MS (ES) m/z 458.2.

Example 93

2-(methylsulfonyl)-2,3-dihydropyrano[3,2-e]isoindol-1(7H)-one (95)

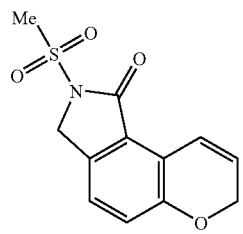

To a solution of 2,3-dihydropyrano[3,2-e]isoindol-1(7H)-one (71) (500 mg, 2.67 mmol) in THF (35 ml) was added NaH (95%, 87 mg, 3.47 mmol) in portions. Resulting mixture was stirred for 40 min before adding MeSO$_2$Cl by syringe. Stirring was continued for 1 hour. The solvent was removed in vacuo and the residue was portioned with CH$_2$Cl$_2$. The organic solution was washed with H$_2$O, sat. NaCl and dried over Na$_2$SO4. Concentration in vacuo gave the title compound (95) as a solid (490 mg, 69%). MS (ES) m/z 266.0.

Example 94

Testing Affinity of Compounds for the 5-HT Transporter

A protocol similar to that used by Cheetham et al. (*Neuropharmacol.*, 1993, 32: 737) was used to determine the affinity of the compounds of the invention for the serotonin transporter. The compound's ability to displace $^3$H-paroxetine from male rat cortical membranes was determined using a Tom Tech filtration device to separate bound from free $^3$H-paroxetine and Wallac 1205 Beta Plate® counter to quantitate bound radioactivity. K$_i$s thus determined for standard clinical antidepressants are 1.96 nM for fluoxetine, 14.2 nM for imipramime and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OH-DPAT (dipropylaminotetralin) from the 5-HT$_{1A}$ serotonin receptor following a modification of the procedure of Hall et al., (*J. Neurochem.*, 1985, 44: 1685) which utilizes CHO cells stably transfected with human 5-HT$_{1A}$ receptors. The 5-HT$_{1A}$ affinities for the compounds of the invention are reported below as K$_i$s.

The agonist or antagonist activity at 5-HT$_{1A}$ receptors was established by using two different assays. The $^{35}$S-GTPγS binding assay similar to that used by Lazareno and Birdsall (*Br. J. Pharmacol.*, 1993, 109: 1120) was used to determine the test compound's ability to affect the binding of $^{35}$S-GTPγS to membranes containing cloned human 5-HT$_{1A}$ receptors. Agonists produce an increase in binding whereas antagonists produce no increase but rather reverse the effects of the standard agonist 8-OH-DPAT. The test compound's maximum stimulatory effect is represented as the E$_{max}$, while its potency is defined by the EC$_{50}$. The test compound's maximum inhibitory effect is represented as the I$_{max}$, while its potency is defined by the IC$_{50}$. The second assay measured cAMP accumulation upon binding of the ligand to the 5-HT$_{1A}$ receptor. Antagonists block the effect of the standard agonist 8-OH-DPAT resulting in an increase in cAMP accumulation while agonists have the reverse effect. The test compound's maximum stimulatory or inhibitory effect is represented as the E$_{max}$ while its potency is defined by either IC$_{50}$ for an antagonist or EC$_{50}$ for an agonist. [$^3$H]-8-OH-DPAT was used to determine maximum agonist or antagonist response in both functional assays.

The results of the three standard experimental test procedures described above were as follows:

Example 95

8-OH-DPAT Binding in CHO Cells Stabily Transfected with Human 5HT1a Receptor.

MATERIALS AND METHODS: Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4 C) in buffer (50 mM Tris pH 7.5). The resulting pellets are aliquoted and placed at −80 C. On day of assay, the cells are thawed on ice, and resuspended in buffer. The binding assay is performed in a 96 well microtiter plate in a total volume of 250 mL.

Non-specific binding is determined in the presence of 10 mM 5HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM. Subsequently, $K_i$ values are determined for compounds defined to be active.

MEASUREMENTS: Percent Inhibition
$K_i$—as determined by RFComp (Lundon Software)
REFERENCE COMPOUNDS: Serotonin
8-OH-DPAT Example 96 cAMP RIA in CHO Cell Stabily Transfected with the h5HT1a Receptor.

MATERIALS AND METHODS: Stably transfected CHO cells are grown in DMEM containing 10% heat inactivated FBS and non-essential amino acids. The cells are plated at a density of ×10(6) cells per well in a 24 well plate and incubated for 2 days in a CO2 incubator. On the second day, the media is replaced with 0.5 ml treatment buffer (DMEM+25 mM HEPES, 5 mM theophylline, 10 µM pargyline) and incubated 10 minutes at 37 C. Wells are treated with forskolin (1 µM final conc) followed immediately by test compound (0.1 and 1 µM for initial screen) and incubated for an additional 10 min at 37 C. Reaction is terminated by removal of the media and addition of 0.5 ml ice cold assay buffer (supplied in RIA kit). Plates are stored at −20 C. prior to assessment of cAMP formation by RIA. Compounds shown to have no agonist activities are further analyzed for ability to reverse agonist activity. In separate experiments, 6 concentrations of antagonist are preincubated for 20 min prior to the addition of agonist and forskolin. Cells are harvested as described. The cAMP kit is supplied by Amersham and the RIA is performed as per kit instructions.

MEASUREMENTS: Initial Screen—Percent inhibition of forskolin stimulated cAMP
Secondary screen—IC50 of reversal of agonist activity.
CALCULATIONS: Calculations of IC50 performed by GraphPad Prism
REFERENCE COMPOUNDS: Serotonin
Buspirone Example 97

$^3$H-Paroxetine Binding to Assess Affinity of Drugs for the Serotonin Transporter:

A protocol similar to that used by Cheetham et al. (Neuropharmacol. 32:737, 1993) was used to determine the affinity of compounds for the serotonin transporter. Briefly, frontal cortical membranes prepared from male S.D. rats were incubated with $^3$H-paroxetine (0.1 nM) for 60 min at 25° C. All tubes also contained either vehicle, test compound (one to eight concentrations), or a saturating concentration of fluoxetine (10 µM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Non-linear regression analysis was used to determine $IC_{50}$ values which were converted to Ki values using the method of Cheng and Prusoff (Biochem. Pharmacol. 22: 3099, 1973); Ki=IC50/((Radioligand conc.)/(1+KD)).

Like the antidepressants fluoxetine, paroxetine and sertraline, the compounds of this invention have the ability to block the reuptake of the brain neurotransmitter serotonin. They are thus useful for the treatment of diseases commonly treated by the administration of serotonin selective reuptake inhibitor (SSRI) antidepressants, such as depression, (including but not limited to major depressive disorder, childhood depression and dysthymia), anxiety, panic disorder, post-traumatic stress disorder, premenstrual dysphoric disorder (also known as premenstrual syndrome), attention deficit disorder (with and without hyperactivity), obsessive compulsive disorder, social anxiety disorder, generalized anxiety disorder, obesity, eating disorders such as anorexia nervosa, bulimia nervosa, vasomotor flushing, cocaine and alcohol addiction, sexual dysfunction, cognitive deficits resulting from neurodegenerative disorders like Alzheimer's disease, and related illnesses. Moreover, some of the compounds of this invention have potent affinity for and antagonist activity at brain 5-$HT_{1A}$ serotonin receptors. Fairly recent clinical trials employing drug mixtures (e.g. fluoxetine and pindolol) have demonstrated a more rapid onset of antidepressant efficacy for a treatment combining SSRI activity and 5-$HT_{1A}$ antagonism (Blier and Bergeron, *J. Clin. Psychopharmacol.*, 1995, 15(3): 217-22; F. Artigas et al., *Trends Neurosci.*, 1996, 19(9): 378-83; Tome et al., *J. Affect Disord.*, 1997, 44(2-3): 101-9). The compounds of this invention are thus interesting and useful for treating depressive illnesses.

When ranges are used herein for physical properties, such as molecular weight, or chemical properties, such as chemical formulae, all combination and subcombinations of ranges of specific embodiments therein are intended to be included.

The disclosure of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of the Formula (I):

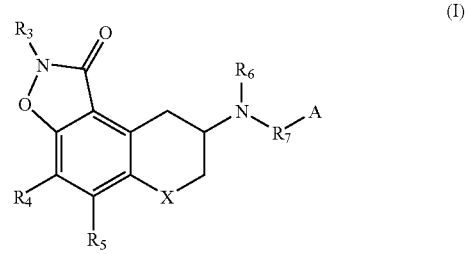

or a pharmaceutically acceptable salt thereof or stereoisomer thereof,
wherein
$R_3$ is a hydrogen, hydroxyl, halogen, —($C_1$-$C_3$)-alkyl, —O—($C_1$-$C_3$)-alkyl, —($C_3$-$C_6$)-cycloalkyl, —$SO_2R_{20}$, or —$COR_{20}$, wherein —$(C_1$-$C_3)$-alkyl, —O—$(C_1$-$C_3)$-alkyl, or —$(C_3$-$C_6)$-cycloalkyl are optionally branched, $R_4$ and $R_5$ are each independently hydrogen, hydroxyl, linear or branched —$(C_1$-$C_6)$-alkyl, linear or branched —$(C_2$-$C_6)$-alkenyl, halogen, —$COR_{14}$, —$OR_{14}$, —$SR_{14}$, —$SO_2NR_{14}R_{15}$, —$NO_2$, —$CONR_{14}R_{15}$ or —$(C_3$-$C_6)$-cycloalkyl, which optionally contains a nitrogen, oxygen or sulfur atom, $R_6$ is hydrogen, a linear or branched —$(C_1$-$C_6)$-alkyl or a linear or branched —$(CH_2)_m$—B, the —$(C_1$-$C_6)$-alkyl or —$(CH_2)_m$—B which may optionally be substituted with at least one nitrogen or oxygen atom provided that $R_6$ has at least two carbon atoms in sequence directly attached to the nitrogen of Formula (I), wherein B is a $(C_3$-$C_5)$-cycloalkyl, a saturated, partially saturated or aromatic $(C_5$-$C_7)$-carbocyclic ring or a phenyl fused to a saturated, partially saturated or aromatic $(C_5$-$C_7)$-carbocyclic ring, wherein the cycloalkyl, phenyl or carbocyclic ring is optionally substituted by one to two substituents per ring, wherein said substituents are independently selected from the group consisting of halogen, cyano, —$(C_1$-$C_6)$-alkyl, —$(C_2$-$C_6)$-alkenyl, —$(C_2$-$C_6)$-alkynyl, —$(C_3$-$C_7)$-carbocycle, —$(C_1$-$C_6)$-alkoxy, —$OCF_3$, —$(C_6$-$C_{10})$-aryl and —$(C_2$-$C_9)$-heterocycle; further wherein one or two ring atoms in the cycloalkyl, phenyl or carbocyclic ring may optionally be replaced by nitrogen, oxygen or sulfur, and m is a number from 0 to 7;

$R_7$ is selected from linear or branched —$(C_1$-$C_6)$-alkylene-, linear or branched —$(C_2$-$C_6)$-alkenylene- or —$(CH_2)_p$—$C_3$-$C_6)$-cycloalkyl-$(CH_2)_q$—, each of which is optionally substituted with a halogen or hydroxyl, wherein at least one ring atom of the —$(C_3$-$C_6)$-cycloalkyl is optionally replaced with a nitrogen, sulfur or oxygen, and at least two ring atoms of the alkylene, alkenylene or cycloalkyl are carbon atoms, and p and q are each independently 0, 1 or 2;

Q is selected from —$(C_1$-$C_3)$-alkylene-, —O—$(C_1$-$C_2)$-alkylene-, —$(C_2$-$C_3)$-alkenylene-, or —O—$(C_2)$-alkenylene-, wherein the alkylene or alkenylene is optionally substituted with a —$(C_1$-$C_3)$-alkyl or a halogen, and wherein for —O—$(C_1$-$C_2)$-alkylene- or —O—$(C_2$-$C_3)$-alkenylene-, the O is directly attached to the phenyl ring;

A is

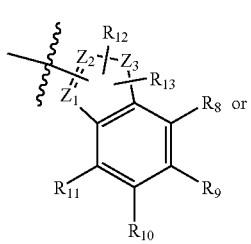

(A₁)

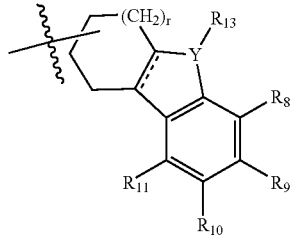

(A₂)

$R_6$, $R_8$, $R_9$, $R_{10}$, and $R_{11}$ are each independently hydrogen, cyano, carboxamido, carboalkoxy, trifluoromethyl, hydroxyl, linear or branched —$(C_1$-$C_6)$-alkyl, linear or branched —$(C_2$-$C_6)$-alkenyl, halogen, —$OCF_3$, alkanoyloxy, alkanamido, alkanesulfonyl, alkanesulfonamido, phenyl, —$NR_{16}R_{17}$—, —$COR_{16}$, —$OR_{16}$, —$SR_{16}$, —$OR_{16}$, or —$NO_2$, X and Y are each independently —$CR_{18}R_{19}$—, —O—, —$NR_{18}$— or —S—;

$Z_1$ is carbon or nitrogen, $Z_2$ is carbon and $Z_3$ is carbon, nitrogen, oxygen or sulfur; wherein at least one of $Z_1$ and $Z_3$ is not carbon, wherein a double bond is optionally present between $Z_1$ and $Z_2$, wherein $A_1$ is attached to $R_7$ through $Z_1$, $Z_2$ or $Z_3$ except when $Z_3$ is oxygen, and further wherein when $R_7$ is linked to $Z_3$, then $Z_3$ is nitrogen;

$R_{12}$ and $R_{13}$ are each independently hydrogen or a linear or branched —$(C_1$-$C_6)$-alkyl, wherein $R_{12}$ and $R_{13}$ may be attached at any of $Z_1$, $Z_2$ or $Z_3$, and further wherein $R_{13}$ is optionally present at $Z_1$ or $Z_2$ when $Z_3$ is oxygen;

$R_{14}$, $R_{15}$, $R_{16}$, $R_{17}$, $R_{18}$ and $R_{19}$ are each independently hydrogen, hydroxyl, halogen, a linear or branched $(C_1$-$C_6)$-alkyl or a linear or branched $(C_2$-$C_6)$-alkenyl;

$R_{20}$ is a hydrogen, a linear or branched $(C_1$-$C_6)$-alkyl or a $(C_3$-$C_7)$-cycloalkyl;

and the dotted lines represent optional double bonds.

2. The compound according to claim 1 of Formula (I), wherein Y is —NH—.

3. The compound according to claim 1 of Formula (I), wherein Y is —O—.

4. The compound according to claim 1 of Formula (I), wherein X is —O—.

5. The compound according to claim 1 of Formula (I), wherein $R_6$ is —$(CH_2)_m$—B, m is 0 or 1, and B is a $C_3$-$C_6$-cycloalkyl.

6. The compound according to claim 1 of Formula (I), wherein $R_6$ is a linear $C_2$-$C_4$-alkyl.

7. The compound according to claim 1 of Formula (I), wherein $R_6$ is a branched $C_3$-$C_5$-alkyl.

8. The compound according to claim 1 of Formula (I), wherein $R_6$ is —$(CH_2)_m$—B, m is 0 or 1, and B is an aromatic $(C_5$-$C_7)$-carbocyclic ring or a phenyl fused to a saturated, partially saturated or aromatic $(C_5$-$C_7)$-carbocyclic ring.

9. The compound according to claim 8 of Formula (I), wherein the $(C_5$-$C_7)$-carbocyclic ring comprises a —O—.

10. The compound according to claim 8 of Formula (I), wherein $R_6$ is —$(CH_2)_m$—B, m is 2, 3 or 4, and B is a phenyl fused to a saturated, partially saturated or aromatic $(C_5$-$C_7)$-carbocyclic ring.

11. The compound according to claim 10 of Formula (I), wherein the $(C_5$-$C_7)$-carbocyclic ring comprises a —NH—.

12. The compound according to claim 11 of Formula (I), wherein the ($C_5$-$C_7$)-carbocyclic ring is substituted with at least one fluorine atom.

13. The compound according to claim 1 of Formula (I), wherein A is

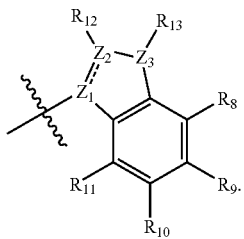

14. The compound according to claim 13 of Formula (I), wherein $Z_3$ is —N—.

15. The compound according to claim 1 of Formula (I), wherein A is

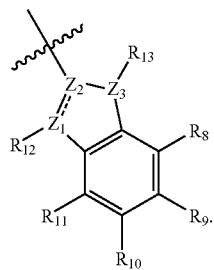

16. The compound according to claim 15 of Formula (I), wherein $Z_3$ is —N—.

17. The compound according to claim 1 of Formula (I), wherein A is

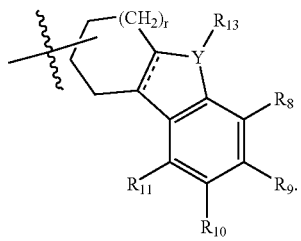

18. The compound according to claim 17 of Formula (I), wherein Y is —NH—.

19. The compound according to any claim 1 of Formula (I), wherein $R_7$ is a linear $C_1$-$C_4$ alkyl.

20. The compound according to claim 1 of Formula (I), wherein at least one of $R_5$, $R_8$, $R_9$, $R_{10}$ and $R_{11}$ is fluorine.

21. The compound according to claim 1 of Formula (I), wherein $R_3$ is —$CH_3$.

22. The compound according to claim 1 of Formula (I), wherein Q is —$CH_2$— or —($CH_2$)$_2$—.

23. The compound according to claim 1 of Formula (I), wherein Q is —O—($CH_2$)—or —O—($CH_2$)$_2$—.

24. The compound according to claim 1 of Formula (I), wherein Q is —$CH_2$=$CH_2$— or —O—$CH_2$=$CH_2$—.

25. The compound according to claim 1 of Formula (I), wherein $R_4$ or $R_5$ is —O—$CH_2$ or —$NO_2$.

26. The compound according to claim 1 of Formula (I), wherein $R_7$ is

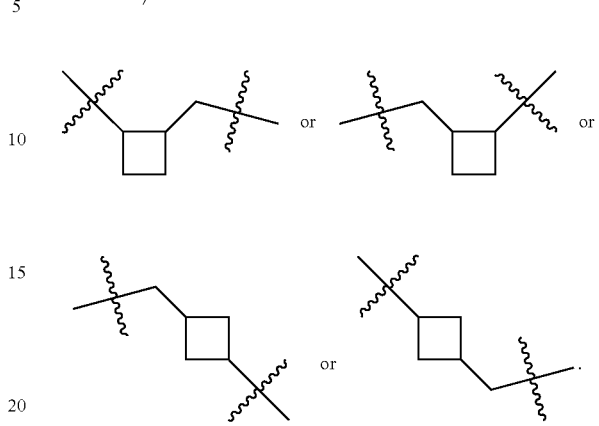

27. The compound according to claim 1 of Formula (I), wherein $R_7$ is —($CH_3$)$_p$—($C_3$-$C_6$)-cycloalkyl-($CH_3$)$_q$—, and p and q are not both 0.

28. The compound according to claim 1 of Formula (I), wherein $R_{10}$ is a nitrile group.

29. The compound according to claim 13 of Formula (I), wherein A is

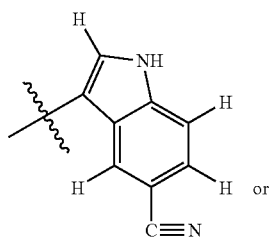

or

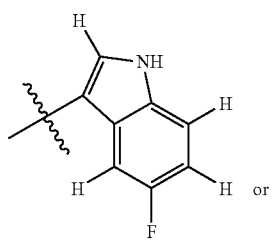

or

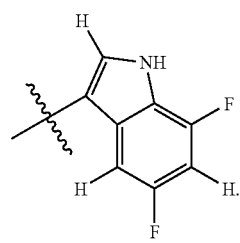

30. The compound according to claim 13 of Formula (I), wherein A is

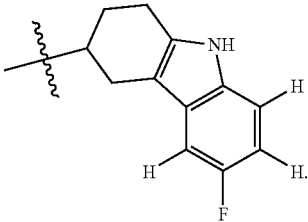

31. A compound according to claim 1, of Formula (Ia):

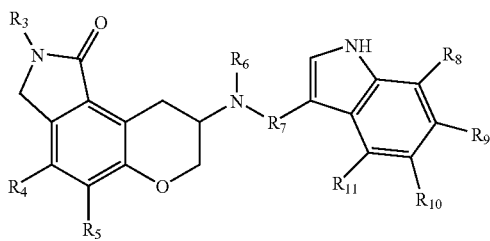

wherein $R_3$, $R_4$, $R_5$, $R_6$, $R_7$, $R_8$, $R_9$, $R_{10}$ and $R_{11}$, are as previously defined.

32. A compound according to claim 1, of Formula (Ib):

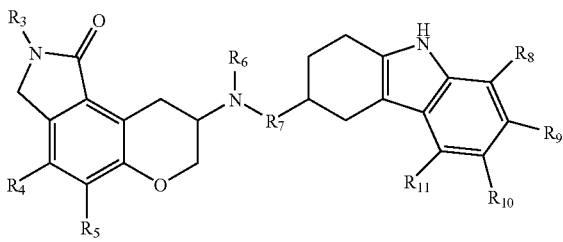

wherein $R_3$, $R_4$, $R_5$, $R_6$, $R_7$, $R_8$, $R_9$, $R_{10}$ and $R_{11}$, are as previously defined.

33. A compound according to claim 1, wherein the compound is:
- 8-{[3-(5-fluoro-1H-indol-3-yl)propyl]amino}-2,3,8,9-tetrahydropyrano[3,2-e]isoindol-1(7H)-one;
- (8S)-8-{[3-(5-fluoro-1H-indol-3-yl)propyl]amino}-2,3,8,9-tetrahydropyrano[3,2-e]isoindol-1(7H)-one;
- (8R)-8-{[3-(5-fluoro-1H-indol-3-yl)propyl]amino}-2,3,8,9-tetrahydropyrano[3,2-e]isoindol-1(7H)-one;
- 8-{(cyclopropylmethyl)[3-(5-fluoro-1H-indol-3-yl)propyl]amino}-2,3,8,9-tetrahydropyrano[3,2-e]isoindol-1(7H)-one;
- (8S)-8-{(cyclopropylmethyl)[3-(5-fluoro-1H-indol-3-yl)propyl]amino}-2,3,8,9-tetrahydropyrano[3,2-e]isoindol-1(7H)-one;
- (8R)-8-{(cyclopropylmethyl)[3-(5-fluoro-1H-indol-3-yl)propyl]amino}-2,3,8,9-tetrahydropyrano[3,2-e]isoindol-1(7H)-one;
- 8-{cyclobutyl[3-(5-fluoro-1H-indol-3-yl)propyl]amino}-2,3,8,9-tetrahydropyrano[3,2-e]isoindol-1(7H)-one;
- 8-{(cyclobutylmethyl)[3-(5-fluoro-1H-indol-3-yl)propyl]amino}-2,3,8,9-tetrahydropyrano[3,2-e]isoindol-1(7H)-one;
- 8-{(cyclobutylmethyl)[3-(5-fluoro-1H-indol-3-yl)propyl]amino}-2,3,8,9-tetrahydropyrano[3,2-e]isoindol-1(7H)-one;
- 8-[[3-(5-fluoro-1H-indol-3-yl)propyl](methyl)amino]-2,3,8,9-tetrahydropyrano[3,2-e]isoindol-1(7H)-one
- 8-{ethyl[3-(5-fluoro-1H-indol-3-yl)propyl]amino}-2,3,8,9-tetrahydropyrano[3,2-e]isoindol-1(7H)-one;
- 8-[[3-(5-fluoro-1H-indol-3-yl)propyl](isobutyl)amino]-2,3,8,9-tetrahydropyrano[3,2-e]isoindol-1(7H)-one;
- 8-{(cyclohexylmethyl)[3-(5-fluoro-1H-indol-3-yl)propyl]amino}-2,3,8,9-tetrahydropyrano[3,2-e]isoindol-1(7H)-one;
- 8-{benzyl[3-(5-fluoro-1H-indol-3-yl)propyl]amino}-2,3,8,9-tetrahydropyrano[3,2-e]isoindol-1(7H)-one;
- 8-[[3-(5-fluoro-1H-indol-3-yl)propyl](3-furylmethyl)amino]-2,3,8,9-tetrahydropyrano[3,2-e]isoindol-1(7H)-one;
- 8-{[3-(5,7-difluoro-1H-indol-3-yl)propyl]amino}-2,3,8,9-tetrahydropyrano[3,2-e]isoindol-1(7H)-one;
- 8-{cyclobutyl[3-(5,7-difluoro-1H-indol-3-yl)propyl]amino}-2,3,8,9-tetrahydropyrano[3,2-e]isoindol-1(7H)-one;
- 3-{3-[(1-oxo-1,2,3,7,8,9-hexahydropyrano[3,2-e]isoindol-8-yl)amino]propyl}-1H-indole-5-carbonitrile;
- 3-{3-[(cyclopropylmethyl)(1-oxo-1,2,3,7,8,9-hexahydropyrano[3,2-e]isoindol-8-yl)amino]propyl}-1H-indole-5-carbonitrile;
- 3-(3-{(cyclopropylmethyl)[(8S)-1-oxo-1,2,3,7,8,9-hexahydropyrano[3,2-e]isoindol-8-yl]amino}propyl)-1H-indole-5-carbonitrile;
- 3-(3-{(cyclopropylmethyl)[(8R)-1-oxo-1,2,3,7,8,9-hexahydropyrano[3,2-e]isoindol-8-yl]amino}propyl)-1H-indole-5-carbonitrile;
- 8-{[4-(5-fluoro-1H-indol-3-yl)butyl]amino}-2,3,8,9-tetrahydropyrano[3,2-e]isoindol-1(7H)-one;
- 8-{(cyclopropylmethyl)[4-(5-fluoro-1H-indol-3-yl)butyl]amino}-2,3,8,9-tetrahydropyrano[3,2-e]isoindol-1(7H)-one;
- 8-{[(6-fluoro-2,3,4,9-tetrahydro-1H-carbazol-3-yl)methyl]amino}-2,3,8,9-tetrahydropyrano[3,2-e]isoindol-1(7H)-one;
- 8-{[3-(5-fluoro-1H-indol-3-yl)propyl]amino}-2-methyl-2,3,8,9-tetrahydropyrano[3,2-e]isoindol-1(7H)-one;
- 8-{(cyclopropylmethyl)[3-(5-fluoro-1H-indol-3-yl)propyl]amino}-2-methyl-2,3,8,9-tetrahydropyrano[3,2-e]isoindol-1(7H)-one;
- (8S)-8-{(cyclopropylmethyl)[3-(5-fluoro-1H-indol-3-yl)propyl]amino}-2-methyl-2,3,8,9-tetrahydropyrano[3,2-e]isoindol-1(7H)-one;

(8R)-8-{(cyclopropylmethyl)[3-(5-fluoro-1H-indol-3-yl)propyl]amino}-2-methyl-2,3,8,9-tetrahydropyrano[3,2-e]isoindol-1(7H)-one;

8-[[3-(5-fluoro-1H-indol-3-yl)propyl](methyl)amino]-2-methyl-2,3,8,9-tetrahydropyrano[3,2-e]isoindol-1(7H)-one;

8-{ethyl[3-(5-fluoro-1H-indol-3-yl)propyl]amino}-2-methyl-2,3,8,9-tetrahydropyrano[3,2-e]isoindol-1(7H)-one;

8-[[3-(5-fluoro-1H-indol-3-yl)propyl](isobutyl)amino]-2-methyl-2,3,8,9-tetrahydropyrano[3,2-e]isoindol-1(7H)-one;

8-{cyclobutyl[3-(5-fluoro-1H-indol-3-yl)propyl]amino}-2-methyl-2,3,8,9-tetrahydropyrano[3,2-e]isoindol-1(7H)-one;

8-{(cyclobutylmethyl)[3-(5-fluoro-1H-indol-3-yl)propyl]amino}-2-methyl-2,3,8,9-tetrahydropyrano[3,2-e]isoindol-1(7H)-one;

3-{3-[(2-methyl-1-oxo-1,2,3,7,8,9-hexahydropyrano[3,2-e]isoindol-8-yl)amino]propyl}-1H-indole-5-carbonitrile;

3-{3-[(cyclopropylmethyl)(2-methyl-1-oxo-1,2,3,7,8,9-hexahydropyrano[3,2-e]isoindol-8-yl)amino]propyl}-1H-indole-5-carbonitrile;

8-{[3-(5,7-difluoro-1H-indol-3-yl)propyl]amino}-2-methyl-2,3,8,9-tetrahydropyrano[3,2-e]isoindol-1(7H)-one;

8-{(cyclopropylmethyl)[3-(5,7-difluoro-1H-indol-3-yl)propyl]amino}-2-methyl-2,3,8,9-tetrahydropyrano[3,2-e]isoindol-1(7H)-one;

8-{[(6-fluoro-2,3,4,9-tetrahydro-1H-carbazol-3-yl)methyl]amino}-2-methyl-2,3,8,9-tetrahydropyrano[3,2-e]isoindol-1(7H)-one;

8-{(cyclopropylmethyl)[(6-fluoro-2,3,4,9-tetrahydro-1H-carbazol-3-yl)methyl]amino}-2-methyl-2,3,8,9-tetrahydropyrano[3,2-e]isoindol-1(7H)-one;

8-{cyclobutyl[(6-fluoro-2,3,4,9-tetrahydro-1H-carbazol-3-yl)methyl]amino}-2-methyl-2,3,8,9-tetrahydropyrano[3,2-e]isoindol-1(7H)-one;

9-{[3-(5-fluoro-1H-indol-3-yl)propyl]amino}-3,4,9,10-tetrahydro-2H-pyrano[2,3-h]isoquinolin-1(8H)-one;

9-[[3-(5-fluoro-1H-indol-3-yl)propyl](methyl)amino]-3,4,9,10-tetrahydro-2H-pyrano[2,3-h]isoquinolin-1(8H)-one;

9-{ethyl[3-(5-fluoro-1H-indol-3-yl)propyl]amino}-3,4,9,10-tetrahydro-2H-pyrano[2,3-h]isoquinolin-1(8H)-one;

9-[[3-(5-fluoro-1H-indol-3-yl)propyl](propyl)amino]-3,4,9,10-tetrahydro-2H-pyrano[2,3-h]isoquinolin-1(8H)-one;

9-[[3-(5-fluoro-1H-indol-3-yl)propyl](isobutyl)amino]-3,4,9,10-tetrahydro-2H-pyrano[2,3-h]isoquinolin-1(8H)-one;

9-{(cyclopropylmethyl)[3-(5-fluoro-1H-indol-3-yl)propyl]amino}-3,4,9,10-tetrahydro-2H-pyrano[2,3-h]isoquinolin-1(8H)-one;

9-{cyclobutyl[3-(5-fluoro-1H-indol-3-yl)propyl]amino}-3,4,9,10-tetrahydro-2H-pyrano[2,3-h]isoquinolin-1(8H)-one;

9-[[3-(5-fluoro-1H-indol-3-yl)propyl](isopropyl)amino}-3,4,9,10-tetrahydro-2H-pyrano[2,3-h]isoquinolin-1(8H)-one;

9-{benzyl[3-(5-fluoro-1H-indol-3-yl)propyl]amino}-3,4,9,10-tetrahydro-2H-pyrano[2,3-h]isoquinolin-1(8H)-one;

9-[[3-(5-fluoro-1H-indol-3-yl)propyl](pyridin-4-ylmethyl)amino]-3,4,9,10-tetrahydro-2H-pyrano[2,3-h]isoquinolin-1(8H)-one;

9-[[3-(5-fluoro-1H-indol-3-yl)propyl](3,3,3-trifluoropropyl)amino]-3,4,9,10-tetrahydro-2H-pyrano[2,3-h]isoquinolin-1(8H)-one;

6-fluoro-9-{[3-(5-fluoro-1H-indol-3-yl)propyl]amino}-3,4,9,10-tetrahydro-2H-pyrano[2,3-h]isoquinolin-1(8H)-one;

9-{(cyclopropylmethyl)[3-(5-fluoro-1H-indol-3-yl)propyl]amino}-6-fluoro-3,4,9,10-tetrahydro-2H-pyrano[2,3-h]isoquinolin-1(8H)-one; or 9-{ethyl[3-(5-fluoro-1H-indol-3-yl)propyl]amino}-6-fluoro-3,4,9,10-tetrahydro-2H-pyrano[2,3-h]isoquinolin-1(8H)-one;

8-{Cyclopropylmethyl-[3-(5-fluoro-3-methyl-2,3-dihydro-1H-indol-3-ylmethyl)-cyclobutyl]-amino}-5-methoxy-2,3,8,9-tetrahydro-7H-pyrano[3,2-e]isoindol-1-one; or 8-{Cyclopropylmethyl-[3-(5-fluoro-3-methyl-2,3-dihydro-1H-indol-3-ylmethyl)-cyclobutyl]-amino}-5-fluoro-2,3,8,9-tetrahydro-7H-pyrano[3,2-e]isoindol-1-one;

8-{Cyclopbutylmethyl-[3-(5-fluoro-3-methyl-2,3-dihydro-1H-indol-3-ylmethyl)-cyclobutyl]-amino}-5-methoxy-2,3,8,9-tetrahydro-7H-pyrano[3,2-e]isoindol-1-one; and 8-{Cyclobutylmethyl-[3-(5-fluoro-3-methyl-2,3-dihydro-1H-indol-3-ylmethyl)-cyclobutyl]-amino}-5-fluoro-2,3,8,9-tetrahydro-7H-pyrano[3,2-e]isoindol-1-one, or a pharmaceutically acceptable salt thereof.

34. A pharmaceutical composition comprising at least one compound according to claim 1 of Formula (I) and a pharmaceutically acceptable carrier therefore.

35. A pharmaceutical composition comprising at least one compound according to claim 33 and a pharmaceutically acceptable carrier therefore.

36. A method of making a compound according to claim 1 of Formula (I), wherein said method comprises (a) combining a compound of formula (III)

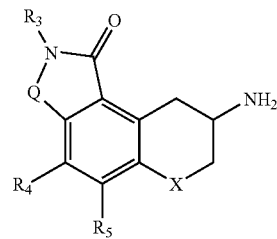

with a compound of formula (VIII)

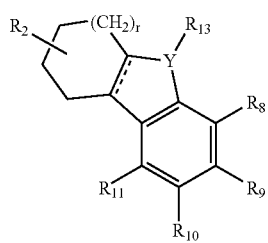

wherein $R_2$ is the corresponding amine of $R_7$, under conditions sufficient for reductive amination;

(b) combining the product of (a) with a compound of formula $R_6CHO$ under conditions for reductive amination, to obtain a compound of formula (IX)

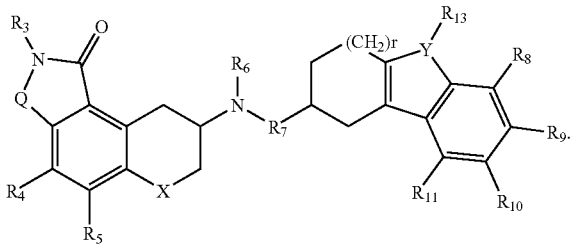

37. A compound according to claim 1, of Formula (Ic):

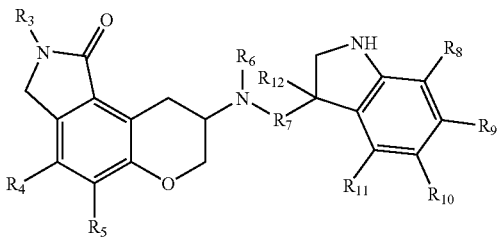

wherein $R_3$, $R_1$, $R_5$, $R_6$, $R_7$, $R_8$, $R_9$, $R_{10}$, $R_{11}$ and $R_{12}$ are as previously defined.

38. The compound of claim 37, wherein at least one $R_3$, $R_4$, $R_5$, $R_6$, $R_7$, $R_8$, $R_9$, $R_{10}$ and $R_{11}$ are defined as follows: $R_3$, $R_4$, $R_8$, $R_9$ and $R_{11}$ are hydrogen; $R_5$ is —$OCH_3$ or fluorine; $R_6$ is —$(CH_2)_m$—B, with —B being a —$(C_3$-$C_5)$-cycloalkyl; $R_7$ is —$(CH_2)_p$—$(C_3$-$C_6)$-cycloalkyl-$(CH_2)_q$; $R_{10}$ is a halogen; and $R_{12}$ is a —$(C_1$-$C_6)$-alkyl.

39. The compound of claim 38, wherein for B, p is 0 and q is 1 or p is 1 and q is 0, and the cycloalkyl is cyclobutyl.

40. The compound of claim 38, wherein $R_5$ is —$OCH_3$.

41. The compound of claim 38, wherein $R_{10}$ is fluorine.

42. The compound of claim 38, wherein $R_{12}$ is a methyl or ethyl group.

* * * * *